United States Patent
Allwein et al.

(10) Patent No.: US 9,132,128 B2
(45) Date of Patent: Sep. 15, 2015

(54) FUSED BICYCLIC 2,4-DIAMINOPYRIMIDINE DERIVATIVE AS A DUAL ALK AND FAK INHIBITOR

(71) Applicant: Cephalon, Inc., Frazer, PA (US)

(72) Inventors: Shawn P. Allwein, Downingtown, PA (US); Laurent Courvoisier, Thorndale, PA (US); Martin J. Jacobs, Versailles, KY (US); Gregory R. Ott, Media, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 14/474,928

(22) Filed: Sep. 2, 2014

(65) Prior Publication Data

US 2015/0011561 A1    Jan. 8, 2015

Related U.S. Application Data

(63) Continuation of application No. PCT/US2013/029304, filed on Mar. 6, 2013.

(60) Provisional application No. 61/607,305, filed on Mar. 6, 2012.

(51) Int. Cl.
*A61K 31/506* (2006.01)
*C07D 403/04* (2006.01)
*C07D 403/12* (2006.01)

(52) U.S. Cl.
CPC ............ *A61K 31/506* (2013.01); *C07D 403/04* (2013.01); *C07D 403/12* (2013.01)

(58) Field of Classification Search
CPC ... A61K 31/506; C07D 403/04; C07D 403/12
See application file for complete search history.

(56) References Cited

U.S. PATENT DOCUMENTS 8,148,391 B2    4/2012  Ahmed et al.
8,552,186 B2   10/2013  Ahmed et al.

FOREIGN PATENT DOCUMENTS

| WO | WO 2005/009389 | 2/2005 |
| WO | WO 2005/016894 | 2/2005 |
| WO | WO 2005/080393 | 9/2005 |
| WO | WO 2005/097765 | 10/2005 |
| WO | WO 2008051547 A1 * | 5/2008 |

OTHER PUBLICATIONS

J. Zhao et al., 28 Cancer Metastasis Reviews, 35-49, (2009).*
E.L. Kwak et al., 363 New England Journal of Medicine, 1693-1703 (2010).*
R. Piva et al., 107 Blood 689-697 (2006).*
L. Lamant et al., 18 Leukemia, 1693-1698 (2004).*
H. Hermann, 86 Blood, 1694-1700 (1995).*
A Rosenwald et al., 94 Blood, 362-364 (1999).*
G.S. Wood, 88 Blood, 1765-1770 (1996).*
R.E. George et al., 455 Nature, 975-978 (2008).*
J. Cools et al., 34 Genes, Chromosomes & Cancer, 354-362 (2002).*
Armitage et al., "Non-Hodgkin's Lymphoma", *Practice of Oncology*, 6th edition (2001), pp. 2256-2316.
Bagi et al., "Dual Focal Adhesion Kinase/Pyk2 Inhibitor Has Positive Effects on Bone Tumors," *Cancer* (2008) 112, pp. 2313-2321.
Bai et al., "Nucleophosmin-anaplastic lymphoma kinase associated with anaplastic large-cell lymphoma activities the phosphatidylinositol 3-kinase/Akt antiapoptotic signaling pathway," *Blood* (2000) 96, pp. 4319-4327.
Bai et al., "Nucleophosmin-Anaplastic Lymphoma Kinase of Large-Cell Anaplastic Lymphoma is a Constitutively Active Tyrosine Kinase That Utilizes Phospholipase C-γ to Mediate its Mitogenicity," *Mol. Cell. Biol.* (1998) 18, pp. 6951-6961.
Cheng et al., "Anaplastic Lymphoma Kinase as a Therapeutic Target in Anaplastic Large Cell Lymphoma, Non-Small Cell Lung Cancer and Neuroblastoma," *Anticancer Agents in Med. Chem.* (2010) 10, pp. 236-249.
Duyster et al., "Translocations involving anaplastic lymphoma kinase (ALK)," *Oncogene* (2001) 20, pp. 5623-5637.
Ergin et al., "Inhibition of tyrosine kinase activity induces caspase-dependent apoptosis in anaplastic large cell lymphoma with NPM-ALK (p80) fusion protein," *Experimental Hematology* (2001) 29, pp. 1082-1090.
Falini et al., "Lymphomas Expressing ALK Fusion Protein(s) Other Than NPM-ALK," *Blood* (1999) 94, pp. 3509-3515.
Halder et al., "Therapeutic Efficacy of a Novel Focal Adhesion Kinase Inhibitor TAE226 in Ovarian Carcinoma," *Cancer Res.* (2007) 67, pp. 10976-10983.
Halder et al., "Focal Adhesion Kinase Targeting Using In Vivo Short Interfering RNA Delivery in Neutral Liposomes for Ovarian Carcinoma Therapy," *Clin. Cancer Res.* (2006) 12, pp. 4916-4924.
Koivunen et al., "EML4-ALK Fusion Gene and Efficacy of an ALK Kinase Inhibitor in Lung Cancer," *Clin. Cancer Res.* (2008) 14, pp. 4275-4283.
Kornberg et al., "Focal Adhesion Kinase Expression in Oral Cancers," *Head Neck* (1998) 20, pp. 634-639.

(Continued)

*Primary Examiner* — Alexander R Pagano

(57) ABSTRACT

The present invention provides a compound of formula (I)

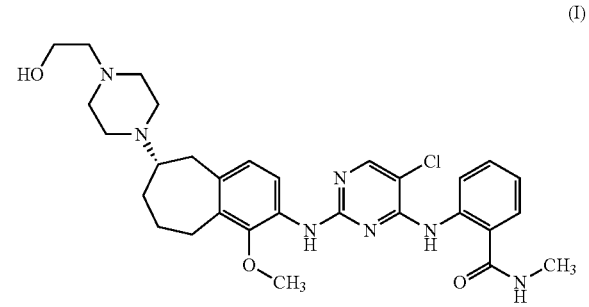

or a salt form thereof. The compound of formula (I) has ALK and FAK inhibitory activity, and may be used to treat proliferative disorders.

20 Claims, 21 Drawing Sheets

(56) References Cited

OTHER PUBLICATIONS

Kuefer et al., "Retrovirus-Mediated Gene Transfer of NPM-ALK Causes Lymphoid Malignancy in Mice," *Blood* (1997) 90, pp. 2901-2910.

Kutok et al., "Molecular Biology of Anaplastic Lymphoma Kinase-Positive Anaplastic Large-Cell Lymphoma," *J. Clin. Oncol.* (2002) 20, pp. 3691-3702.

Kyu-Ho Han et al., "Role of Focal Adhesion Kinase in Human Cancer: A Potential Target for Drug Discovery," *Anti-Cancer Agents in Med. Chem.* (2007) 7, pp. 681-684.

Lawrence et al., "TPM3-ALK and TPM4-ALK Oncogenes in Inflammatory Myofibroblastic Tumors," *Am. J. Pathol.* (2000) 157, pp. 377-384.

Mclean et al., "The Role of Focal-Adhesion Kinase in Cancer—A New Therapeutic Opportunity," *Nat. Rev. Cancer* (2005) 5, pp. 505-515.

Mentlein et al., "Pleiotrophin, an angiogenic and mitogenic growth factor, is expressed in human gliomas," *J. Neurochem.* (2002) 83, pp. 747-753.

Mesaros et al., "Novel 2,3,4,5-tetrahydro-benzo[d]azepine derivatives of 2,4-diaminopyrimidine, selective and orally bioavailable ALK inhibitors with antitumor efficacy in ALCL mouse models," *Bioorg. Med. Chem. Letts.* (2011) 21, pp. 463-466.

Milkiewicz et al., "Inhibitors of anaplastic lymphoma kinase: a patent review," *Expert Opin. Ther. Patents* (2010) 20, pp. 1653-1681.

Mitra et al., "Focal Adhesion Kinase: in Command and Control of Cell Motility," *Nat. Rev. Mol. Cell. Biol.* (2005) 6, pp. 56-68.

Morris et al., "ALK CD30 Lymphomas: A Distinct Molecular Genetic Subtype of Non-Hodgkin's Lymphoma," *Br. J. Haematology* (2001) 113, pp. 275-295.

Ott et al., ALK Chem. Biol. AACR Poster (Nov. 3, 2008).

Ott et al., Med. Chem. Gordon Conf. Poster (Aug. 9, 2009).

Ott et al., "Discovery of a Potent Inhibitor of Anaplastic Lymphoma Kinase with in Vivo Antitumor Activity," *ACS Med. Chem. Lett.* (2010) 1, pp. 493-498.

Owens et al., "Overexpression of the Focal Adhesion Kinase ($p125^{FAK}$) in Invasive Human Tumors," *Cancer Res.* (1995) 55, pp. 2752-2755.

Parsons et al., "Focal Adhesion Kinase: Targeting Adhesion Signaling Pathways for Therapeutic Intervention," *Clin. Cancer Res.* (2008) 14, pp. 627-632.

Powers et al., "Pleiotrophin Signaling Through Anaplastic Lymphoma Kinase is Rate-Limiting for Glioblastoma Growth," *J. Biological Chem.* (2002) 277, pp. 14153-14158.

Roberts et al., "Antitumor Activity and Pharmacology of a Selective Focal Adhesion Kinase Inhibitor, PF-562,271," *Cancer Res.* (2008) 68, pp. 1935-1944.

Slupianek et al., "Role of Phosphatidylinositol 3-Kinase-Akt Pathway in Nucleophosmin/Anaplastic Lymphoma Kinase-mediated Lymphomagenesis," *Cancer Res.* (2001) 61, pp. 2194-2199.

Soda et al., "Identification of the transforming EML4-ALK fusion gene in non-small-cell lung cancer," *Nature* (2007) 448, pp. 561-566.

Stoica et al., "Identification of Anaplastic Lymphoma Kinase as a Receptor for the Growth Factor Pleiotrophin," *J. Biological Chem.* (2001) 276, pp. 16772-16779.

Tremblay et al., "Focal Adhesion Kinase ($pp125^{FAK}$) Expression, Activation and Association with Paxillin and $p50^{CSK}$ in Human Metastatic Prostate Carcinoma," *Int. J. Cancer* (1996) 68, pp. 164-171.

Turturro et al., "Model of Inhibition of the NPM-ALK Kinase Activity by Herbimycin A," *Clin. Cancer Res.* (2002) 8, pp. 240-245.

Weinberg et al., "Fused bicyclic derivatives of 2,4-diaminopyrimidine as c-Met inhibitors," *Bioorg. Med. Chem. Letts.* (2011) 21, pp. 164-167.

Zificsak et al., "2,4-Diaminopyrimidine inhibitors of c-Met kinase bearing benzoxazepine anilines," *Bioorg. Med. Chem. Letts.* (2011) 21, pp. 660-663.

\* cited by examiner

Synthesis of CEP-37440

XRPD Pattern of the CEP-37440 tribenzenesulfonate salt

XRPD Pattern of the CEP-37440 trihydrochloride dihydrate salt

Anti-Tumor Efficacy of CEP-37440 in Sup-M2 ALCL Tumor Xenografts in Mice with Oral Dosing

Body Weights of Mice Bearing Sup-M2 ALCL Tumor Xenografts with CEP-37440 Oral Dosing Plasma and Tumor Levels of CEP-37440 in Mice Bearing Sup-M2 ALCL Tumor Xenografts with Oral Dosing Anti-Tumor Efficacy of CEP-37440 in Karpas-299 Tumor Xenografts in Mouse with Oral Dosing Body Weights of Mice Bearing Karpas-299 Tumor Xenografts with CEP-37440 Oral Dosing Plasma and Tumor Levels of CEP-37440 in Mice Bearing Karpas-299 Tumor Xenografts with Oral Dosing Anti-Tumor Efficacy of CEP-37440 in NCI-H2228 NSCL Tumor Xenografts in Mice with Oral Dosing Anti-Tumor Efficacy of CEP-37440 in NCI-H3122 NSCL Tumor Xenografts in Mice with Oral Dosing Plasma and Tumor Levels of CEP-37440 in Mice Bearing NCI-H2228 NSCL Tumor Xenografts with Oral Dosing Plasma and Tumor Levels of CEP-37440 in Mice Bearing NCI-H3122 NSCL Tumor Xenografts with Oral Dosing Body Weights of Mice Bearing NCI-H2228 NSCL Tumor Xenografts with CEP-37440 Oral Dosing Body Weights of Mice Bearing NCI-H3122 NSCL Tumor Xenografts with CEP-37440 Oral Dosing Anti-Tumor Efficacy and Long Term Tumor Regressions by CEP-37440 in NCI-H2228 NSCL Tumor Xenografts in Mouse Body Weights of Mice Bearing NCI-H2228 NSCL Tumor Xenografts with CEP-37440 Oral Dosing Anti-Tumor Efficacy of CEP-37440 and PF-562271 in Nude Mice Bearing PC-3
Prostate Tumor Xenografts with Constitutive FAK Activation Anti-tumor Efficacy of CEP-37440 and PF-562271 in Nude Mice Bearing HCC-827 Human NSCL Carcinoma Xenografts (EML4-ALK negative)

Body Weights of Nude Mice Bearing HCC-827 Human NSCL Carcinoma Xenografts
(EML4-ALK negative) with CEP-37440 or PF-562271 Oral Dosing Tumor Pharmacodynamic Inhibition of FAK and Anti-tumor Efficacy of CEP-37440 and PF-562271 in SCID Mice Bearing Detroit 562 Human HNSCC Carcinoma Xenografts (EML4-ALK negative)

FUSED BICYCLIC 2,4-DIAMINOPYRIMIDINE DERIVATIVE AS A DUAL ALK AND FAK INHIBITOR

CROSS-REFERENCE TO RELATED APPLICATIONS

This application is a continuation of International Application No. PCT/US2013/029304, filed Mar. 6, 2013, which claims the benefit of U.S. Provisional Application No. 61/607,305, filed Mar. 6, 2012, the disclosures of which are incorporated herein by reference in their entireties.

BACKGROUND OF THE INVENTION

Anaplastic Lymphoma Kinase (ALK) is a cell membrane-spanning receptor tyrosine kinase, which belongs to the insulin receptor subfamily. The most abundant expression of ALK occurs in the neonatal brain, suggesting a possible role for ALK in brain development (Duyster, J. et al., *Oncogene*, 2001, 20, 5623-5637).

ALK is also implicated in the progression of certain tumors. For example, approximately sixty percent of anaplastic large cell lymphomas (ALCL) are associated with a chromosome mutation that generates a fusion protein consisting of nucleophosmin (NPM) and the intracellular domain of ALK. (Armitage, J. O. et al., *Cancer: Principle and Practice of Oncology*, 6$^{th}$ edition, 2001, 2256-2316; Kutok J. L. & Aster J. C., *J. Clin. Oncol.*, 2002, 20, 3691-3702). This mutant protein, NPM-ALK, possesses a constitutively active tyrosine kinase domain that is responsible for its oncogenic property through activation of downstream effectors. (Falini, B. et al., *Blood*, 1999, 94, 3509-3515; Morris, S. W. et al., *Brit. J. Haematol.*, 2001, 113, 275-295; Duyster et al.; Kutok & Aster). In addition, the transforming EML4-ALK fusion gene has been identified in non-small-cell lung cancer (NSCLC) patients (Soda, M., et al., *Nature*, 2007, 448, 561-566) and represents another in a list of ALK fusion proteins that are promising targets for ALK inhibitor therapy. Experimental data have demonstrated that the aberrant expression of constitutively active ALK is directly implicated in the pathogenesis of ALCL and that inhibition of ALK can markedly impair the growth of ALK+ lymphoma cells (Kuefer, Mu et al. *Blood*, 1997, 90, 2901-2910; Bai, R. Y. et al., *Mol. Cell Biol.*, 1998, 18, 6951-6961; Bai, R. Y. et al., *Blood*, 2000, 96, 4319-4327; Ergin, M. et al., *Exp. Hematol.*, 2001, 29, 1082-1090; Slupianek, A. et al., *Cancer Res.*, 2001, 61, 2194-2199; Turturro, F. et al., *Clin. Cancer Res.*, 2002, 8, 240-245). The constitutively activated chimeric ALK has also been demonstrated in about 60% of inflammatory myofibroblastic tumors (IMTs), a slow-growing sarcoma that mainly affects children and young adults. (Lawrence, B. et al., *Am. J. Pathol.*, 2000, 157, 377-384; Duyster et al.).

In addition, ALK and its putative ligand, pleiotrophin, are overexpressed in human glioblastomas (Stoica, G. et al., *J. Biol. Chem.*, 2001, 276, 16772-16779). In mouse studies, depletion of ALK reduced glioblastoma tumor growth and prolonged animal survival (Powers, C. et al., *J. Biol. Chem.*, 2002, 277, 14153-14158; Mentlein, R. et al, *J. Neurochem.*, 2002, 83, 747-753).

An ALK inhibitor would be expected to either permit durable cures when combined with current chemotherapy for ALCL, IMT, proliferative disorders, glioblastoma and possible other solid tumors, or, as a single therapeutic agent, could be used in a maintenance role to prevent cancer recurrence in those patients. Various ALK inhibitors have been reported, such as indazoloisoquinolines (WO 2005/009389), thiazole amides and oxazole amides (WO 2005/097765), pyrrolopyrimidines (WO 2005080393), and pyrimidinediamines (WO 2005/016894).

WO 2008/051547 discloses fused bicyclic derivatives of 2,4-diaminopyrimidine as ALK and c-Met inhibitors. The lead drug candidate disclosed in the '547 application is CEP-28122, a potent ALK inhibitor with oral efficacy against SUP-M2 and Karpas-299 ALK-dependent tumors in mouse xenograft models. CEP-28122 progressed to IND-enabling studies until its development was terminated due to the unexpected occurrence of severe lung toxicity in CEP-28122-treated monkeys.

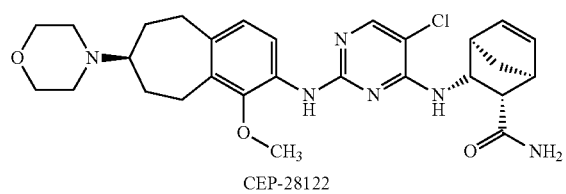

CEP-28122

Focal adhesion kinase (FAK) is an evolutionarily conserved non-receptor tyrosine kinase localized at focal adhesions, sites of cellular contact with the ECM (extra-cellular matrix) that functions as a critical transducer of signaling from integrin receptors and multiple receptor tyrosine kinases, including EGF-R, HER2, IGF-R1, PDGF-R and VEGF-R2 and TIE-2 (Parsons, JT; Slack-Davis, J; Tilghman, R; Roberts, W G. Focal adhesion kinase: targeting adhesion signaling pathways for therapeutic intervention. *Clin. Cancer Res.*, 2008, 14, 627-632; Kyu-Ho Han, E; McGonigal, T. Role of focal adhesion kinase in human cancer—a potential target for drug discovery. *Anti-cancer Agents Med. Chem.*, 2007, 7, 681-684). The integrin-activated FAK forms a binary complex with Src which can phosphorylate other substrates and trigger multiple signaling pathways. Given the central role of FAK binding and phosphorylation in mediating signal transduction with multiple SH2- and SH3-domain effector proteins (Mitra, S K; Hanson, D A; Schlaeper, D D. Focal adhesion kinase: in command and control of cell motility. *Nature Rev. Mol. Cell Biol.*, 2005, 6, 56-68), activated FAK plays a central role in mediating cell adhesion, migration, morphogenesis, proliferation and survival in normal and malignant cells (Mitra et al. 2005; McLean, G W; Carragher, N O; Avizzienyte, E; et al. The role of focal adhesion kinase in cancer—a new therapeutic opportunity. *Nature Reviews Cancer*, 2005, 5, 505-515; and Kyu-Ho Han and McGonigal, 2007). In tumors, FAK activation mediates anchorage-independent cell survival, one of the hallmarks of cancer cells. Moreover, FAK over expression and activation appear to be associated with an enhanced invasive and metastatic phenotype and tumor angiogenesis in these malignancies (Owens, L V; Xu, L; Craven, R J; et al. Over expression of the focal adhesion kinase (p125 FAK) in invasive human tumors. *Cancer Res.*, 1995, 55, 2752-2755; Tremblay, L; Hauck, W. Focal adhesion kinase (pp125FAK) expression, activation and association with paxillin and p50CSK in human metastatic prostate carcinoma. *Int. J. Cancer,* 1996, 68, 164-171; Kornberg, I J. Focal adhesion kinase in oral cancers. *Head and Neck*, 1998, 20: 634-639; Mc Clean et al 2005; Kyu-Ho Han and McGonigal, 2007) and correlated with poor prognosis and shorter metastasis-free survival.

Multiple proof-of-concept studies conducted in various solid tumors using siRNA (Halder, J; Kamat, A A; Landen, C N; et al. Focal adhesion kinase targeting using in vivo short interfering RNA delivery in neutral liposomes for ovarian carcinoma therapy. *Clin. Cancer Res.*, 2006, 12, 4916-4924), dominant-negative FAK, and small molecule FAK inhibitors (Halder, J; Lin, Y G; Merritt, W M; et al. Therapeutic efficacy of a novel focal adhesion kinase inhibitor, TAE226 in ovarian carcinoma. *Cancer Res.*, 2007, 67, 10976-10983; Roberts, W G; Ung, E; Whalen, P; et al. Anti-tumor activity and pharmacology of a selective focal adhesion kinase inhibitor, PF-562, 271. *Cancer Res.*, 2008, 68, 1935-1944; Bagi C M; Roberts G W; and Andersen C J. Dual focal adhesion kinse/Pyk2 inhibitor has positive effects on bone tumors—implications for bone metastases. *Cancer*, 2008, 112, 2313-2321) have provided pre-clinical support for the therapeutic utility of FAK inhibition as an anti-tumor/anti-angiogenic strategy, particularly for androgen-independent prostate cancers, breast cancers, and HNSCCs. In preclinical models of human breast cancer (MDA-MB-231) in nude rats, administration of a small molecule FAK inhibitor (PF-562,271) inhibited primary tumor growth and intra-tibial tumor spread, and restored tumor-induced bone loss (Bagi et al., 2008). Roberts et al., (2008) showed that PF-562,271 inhibited bone metastases, prevented bone resorption, and increased osteogenesis in breast and androgen-independent prostate cancer patients with and without bone metastases, supporting an additional benefit of FAK inhibition in these specific malignancies.

In summary, there is clear genetic and biological evidence that links aberrant ALK activation and constitutive activation of FAK with the onset and progression of certain types of cancer in humans. Considerable evidence indicates that ALK- and FAK-positive tumor cells require these oncogenes to proliferate and survive, and in the case of FAK, to invade and metastasize to distant sites, while inhibition of both ALK and FAK signaling leads to tumor cell growth arrest or apoptosis, resulting in objective cytoreductive effects. Inhibition of FAK also results in attenuation of tumor motility, invasiveness, and metastatic spread, particularly in specific cancers characterized by bone metastatic dissemination and osteolytic disease. FAK activation protects tumor cells from chemotherapy-induced apoptosis, contributing to tumor resistance; modulation of FAK activity (by siRNA or pharmacologically) potentiates efficacy of chemotherapeutic agents in vivo (e.g., doxorubicin, docetaxel and gemcitabine), suggesting the utility for rational combination therapies in specific cancers. ALK and FAK are minimally expressed in most normal tissues in the healthy adult and are activated and/or dysregulated in specific cancers during oncogenesis and/or during early stages of malignant progression. Consequently, the on-target effects of treatment with a dual ALK and FAK inhibitor against normal cells should be minimal, creating a favorable therapeutic index.

A need exists for additional safe and effective ALK and/or FAK inhibitors for the treatment of cancer.

SUMMARY OF THE INVENTION

The present invention provides a compound of formula (I)

(I)

[chemical structure]

or a salt form thereof.

The compound of formula (I) has ALK and FAK inhibitory activity, and may be used to treat ALK- or FAK-mediated disorders or conditions.

The present invention further provides a pharmaceutical composition comprising at least one compound of the present invention together with at least one pharmaceutically acceptable excipient.

DETAILED DESCRIPTION OF THE INVENTION

I. Definitions

Figure 1:
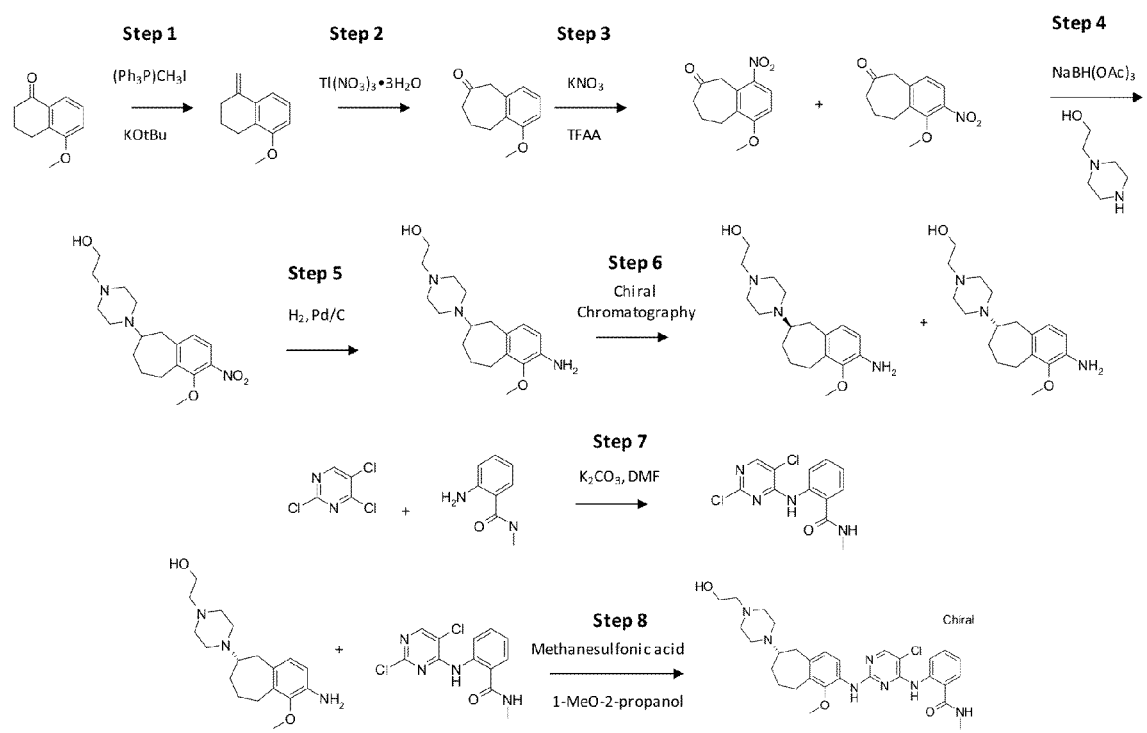
FIG. 1 depicts an schematic overview of a process for preparing CEP-37440.

As used herein, the following terms have the meanings ascribed to them unless specified otherwise.

"Pharmaceutical composition" refers to a composition having a safety/efficacy profile suitable for administration to a human.

"Pharmaceutically acceptable excipient" refers to physiologically tolerable materials, which do not typically produce an allergic or other untoward reaction, such as gastric upset, dizziness and the like, when administered to a human.

"Pharmaceutically acceptable salt" refers to a salt having a safety/efficacy profile suitable for administration to a human.

"Subject" refers to a member of the class Mammalia. Examples of mammals include, without limitation, humans, primates, chimpanzees, rodents, mice, rats, rabbits, horses, livestock, dogs, cats, sheep, and cows.

"Therapeutically effective amount" refers to an amount of a compound sufficient to improve or inhibit worsening of symptoms associated with a disorder or condition being treated in a particular subject or subject population. It should be appreciated that determination of proper dosage forms, dosage amounts, and routes of administration is within the level of ordinary skill in the pharmaceutical and medical arts.

"Treatment" refers to the acute or prophylactic diminishment or alleviation of at least one symptom or characteristic associated or caused by a disorder being treated. For example, treatment can include diminishment of a symptom of a disorder or complete eradication of a disorder.

II. Compound

The present invention provides a compound of formula (I)

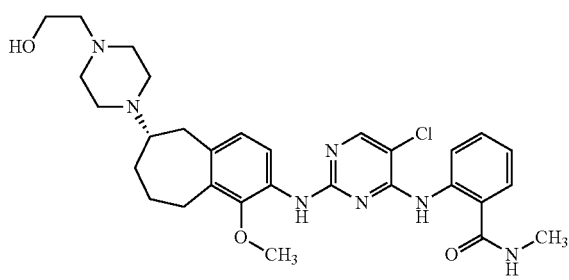

(I)

or a salt form thereof. The compound of formula (I) has the chemical name 2-[[5-chloro-2-[[(6S)-6-[4-(2-hydroxyethyl)piperazin-1-yl]-1-methoxy-6,7,8,9-tetrahydro-5H-benzo[7]annulen-2-yl]amino]pyrimidin-4-yl]amino]-N-methyl-benzamide, and is also known as CEP-37440. We have discovered that the compound of formula (I) possesses surprising and unexpected properties in comparison to CEP-28122 and other related compounds.

The salt form of the compound of formula (I) is preferably pharmaceutically acceptable. Pharmaceutically acceptable acid salt forms of the compound of formula (I) include, but are not limited to, salts derived from inorganic acids such as hydrochloric, nitric, phosphoric, sulfuric, hydrobromic, hydroiodic, phosphorous, and mixtures thereof, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such acid salts thus include, but are not limited to, sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and mixtures thereof. In certain embodiments, the acid salt is chosen from benzenesulfonate and chloride. In certain embodiments the acid salt is a chloride. In certain embodiments, the acid salt is a tribenzenesulfonate. In certain embodiments, the tribenzensulfonate salt is characterized by a XRPD pattern having one or more peaks selected from 7.62, 13.11, 13.76, and 14.05±0.2 degrees 2Θ. In certain embodiments, the tribenzensulfonate salt is characterized by a XRPD pattern having one or more peaks selected from 6.85, 7.62, 8.01, 13.11, 13.76, 14.05, and 14.60±0.2 degrees 2Θ. In certain embodiments, the tribenzensulfonate salt is characterized by a XRPD pattern having one or more peaks selected from 7.62, 13.11, 13.76, 14.05, 17.10, 17.86, and 18.10±0.2 degrees 2Θ. In certain embodiments, the acid salt is a trihydrochloride. In certain embodiments, the acid salt is a trihydrochloride dihydrate. In certain embodiments, the trihydrochloride dihydrate salt is characterized by a XRPD pattern having one or more peaks selected from 5.42, 8.86, 14.06, 17.52 and 18.51±0.2 degrees 2Θ. In certain embodiments, the trihydrochloride dihydrate salt is characterized by a XRPD pattern having one or more peaks selected from 5.42, 5.91, 8.86, 10.80, 11.79, 14.06, 14.72, 17.02, 17.52 and 18.51±0.2 degrees 2Θ. In certain embodiments, the acid salt is a trihydrochloride monohydrate.

The acid addition salts may be prepared by contacting the compound of formula (I) with a sufficient amount of the desired acid to produce the salt in the conventional manner. The free base form of the compound of formula (I) may be regenerated by contacting the salt form with a base and isolating the free base in the conventional manner.

The present invention includes the compound of formula (I) and salt forms thereof in any physical form, including amorphous or crystalline solids in any polymorphic form, in any state of purity. Crystalline polymorphic forms include unsolvated forms as well as solvated forms, such as hydrated forms. Methods of preparing crystalline and amorphous forms of organic compounds such as the compound of formula (I) are well known to those of ordinary skill in the art.

III. Pharmaceutical Composition

The present invention further provides pharmaceutical compositions comprising a compound of the present invention (e.g., a compound of formula (I) or a pharmaceutically acceptable salt thereof), together with a pharmaceutically acceptable excipient. For preparing a pharmaceutical composition from a compound of the present invention, pharmaceutically acceptable excipients can be either solid or liquid. An excipient can be one or more substances which may act as, e.g., a carrier, diluent, flavoring agent, binder, preservative, tablet disintegrating agent, or an encapsulating material. The pharmaceutical composition may contain two or more compounds of the present invention (e.g., two or more different salt forms of the compound of formula (I)). Preferably, the pharmaceutical composition contains a therapeutically effective amount of a compound of formula (I) or a pharmaceutically acceptable salt form thereof. In one embodiment, the composition contains an amount of a compound of formula (I) or a pharmaceutically acceptable salt form thereof effective to treat an ALK- or FAK-mediated disorder or condition. Preferably, a pharmaceutical composition of the present invention will cause a decrease in symptoms or disease indicia associated with an ALK- or FAK-mediated disorder as measured quantitatively or qualitatively. The composition may also contain, in addition to a compound of formula (I) or a pharmaceutically acceptable salt form thereof and a pharmaceutically acceptable excipient, another therapeutic compound, such as a compound useful in the treatment of cancer.

A compound of the present invention can be formulated as a pharmaceutical composition in any form, such as a syrup, an elixir, a suspension, a powder, a granule, a tablet, a capsule, a lozenge, a troche, an aqueous solution, a cream, an ointment, a lotion, a gel, an emulsion, etc. Solid form preparations include powders, tablets, pills, capsules, cachets, suppositories, and dispersible granules. Preferably, the pharmaceutical composition is a tablet or capsule. In one embodiment, the pharmaceutical composition is a tablet. In another embodiment, the pharmaceutical composition is a capsule.

In powders, the excipient may be a finely divided solid in a mixture with a finely divided active component. In tablets, the active component may be mixed with an excipient having the necessary binding properties in suitable proportions and compacted in the shape and size desired. Suitable excipients include magnesium carbonate, magnesium stearate, talc, sugar, lactose, pectin, dextrin, starch, gelatin, tragacanth, methylcellulose, sodium carboxymethylcellulose, low melting wax, cocoa butter, and the like.

The pharmaceutical composition preferably contains from 1% to 95% (w/w) of the active compound. More preferably, the pharmaceutical composition contains from 5% to 70% (w/w) of the active compound.

For preparing suppositories, a low melting wax, such as a mixture of fatty acid glycerides or cocoa butter, may be melted and the active component dispersed homogeneously therein, as by stirring. The molten homogeneous mixture may then be poured into convenient sized molds, allowed to cool, and thereby to solidify.

Liquid form preparations include solutions, suspensions, and emulsions. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Pharmaceutically acceptable excipients are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

The quantity of active component in a pharmaceutical composition may be varied or adjusted from, e.g., 1 mg to 1,000 mg, 5 mg to 500 mg, 10 mg to 300 mg, or 25 mg to 250 mg, according to the particular application.

The dose administered to a subject is preferably sufficient to effect a beneficial therapeutic response in the subject over time. The beneficial dose can vary from subject to subject depending upon, e.g., the subject's condition, body weight, surface area, and side effect susceptibility. Administration can be accomplished via single or divided doses.

IV. Method of Treatment

In another aspect, the present invention provides a method of treating an ALK- or FAK-mediated disorder or condition in a subject comprising: administering to the subject a compound of formula (I) or a pharmaceutically acceptable salt form thereof. In another aspect, the present invention provides a compound of formula (I) or a pharmaceutically acceptable salt form thereof for use in treating an ALK- or FAK-mediated disorder or condition in a subject. In another aspect, the present invention provides a compound of formula (I) or a pharmaceutically acceptable salt form thereof for use in the preparation of a medicament for treating an ALK- or FAK-mediated disorder or condition in a subject. Preferably, the compound of formula (I) or a pharmaceutically acceptable salt form thereof is administered to the subject as a pharmaceutical composition comprising a pharmaceutically acceptable excipient. Preferably, the compound of formula (I) or a pharmaceutically acceptable salt form thereof is administered to the subject in a therapeutically effective amount. In one embodiment, the ALK- or FAK-mediated condition or disorder is cancer. In another embodiment, the ALK- or FAK-mediated condition or disorder is selected from anaplastic large cell lymphoma (ALCL), non-small cell lung cancer (NSCLC), neuroblastoma, glioblastoma, prostate cancer, squamous cell carcinoma (SCC), and breast cancer. In certain embodiments, the ALK- or FAK-mediated condition or disorder is selected from ALK-positive ALCL, EML4-ALK-positive NSCLC, neuroblastoma, glioblastoma, androgen-independent prostate cancers, breast cancers, and head and neck squamous cell carcinomas (HNSCCs). In certain embodiments, the ALK- or FAK-mediated condition or disorder is selected from ALK-positive ALCL, EML4-ALK-positive NSCLC, neuroblastoma, androgen-independent prostate cancers, breast cancers, and HNSCCs. In certain embodiments, the ALK- or FAK-mediated condition or disorder is selected from ALK-positive ALCL, EML4-ALK-positive NSCLC, neuroblastoma, and glioblastoma. In certain embodiments, the ALK- or FAK-mediated condition or disorder is selected from ALK-positive ALCL, EML4-ALK-positive NSCLC, and neuroblastoma. In certain embodiments, the ALK- or FAK-mediated condition or disorder is selected from ALK-positive ALCL and EML4-ALK-positive NSCLC. In certain embodiments, the ALK- or FAK-mediated condition or disorder is selected from androgen-independent prostate cancers, breast cancers, and HNSCCs. In certain embodiments, the ALK- or FAK-mediated condition or disorder is an ALK-mediated condition or disorder. In certain embodiments, the ALK- or FAK-mediated condition or disorder is a FAK-mediated condition or disorder. In certain embodiments, the ALK- or FAK-mediated condition or disorder is a myofibroblastic tumor. In certain embodiments, the ALK- or FAK-mediated condition or disorder is a myofibroblastic tumor with TPM3-ALK or TPM4-ALK oncogenes. In certain embodiments, the ALK- or FAK-mediated condition or disorder is a myofibroblastic tumor with TPM3-ALK oncogenes. In certain embodiments, the ALK- or FAK-mediated condition or disorder is a myofibroblastic tumor with TPM4-ALK oncogenes.

The ALK- or FAK-mediated disorder or condition can be treated prophylactically, acutely, or chronically using compounds of the present invention, depending on the nature of the disorder or condition. Preferably, the subject in each of these methods is human.

In another embodiment, the present invention provides a method of treating a proliferative disorder in a subject, comprising administering to the subject a compound of formula (I) or a pharmaceutically acceptable salt form thereof. In another aspect, the present invention provides a compound of formula (I) or a pharmaceutically acceptable salt form thereof for use in treating a proliferative disorder in a subject. In another aspect, the present invention provides a compound of formula (I) or a pharmaceutically acceptable salt form thereof for use in the preparation of a medicament for treating a proliferative disorder in a subject. Preferably, the compound of formula (I) or a pharmaceutically acceptable salt form thereof is administered to the subject in a pharmaceutical composition comprising a pharmaceutically acceptable excipient. Preferably, the compound of formula (I) or a pharmaceutically acceptable salt form thereof is administered to the subject in a pharmaceutically acceptable amount. In certain embodiments, the proliferative disorder is ALK- or FAK-mediated. In certain embodiments, the proliferative disorder is cancer. In certain embodiments, the proliferative disorder is selected from anaplastic large cell lymphoma (ALCL), non-small cell lung cancer (NSCLC), neuroblastoma, glioblastoma, prostate cancer, squamous cell carcinoma (SCC), and breast cancer. In certain embodiments, the proliferative disorder is selected from ALK-positive ALCL, EML4-ALK-positive NSCLC, neuroblastoma, glioblastoma, androgen-independent prostate cancers, breast cancers, and head and neck squamous cell carcinomas (HNSCCs). In certain embodiments, the proliferative disorder is selected from ALK-positive ALCL, EML4-ALK-positive NSCLC, neuroblastoma, androgen-independent prostate cancers, breast cancers, and HNSCCs. In certain embodiments, the proliferative disorder is selected from ALK-positive ALCL, EML4-ALK-positive NSCLC, neuroblastoma, and glioblastoma. In certain embodiments, the proliferative disorder is selected from ALK-positive ALCL, EML4-ALK-positive NSCLC, and neuroblastoma. In certain embodiments, the proliferative disorder is selected from ALK-positive ALCL and EML4-ALK-positive NSCLC. In certain embodiments, the proliferative disorder is selected from androgen-independent prostate cancers, breast cancers, and HNSCCs.

The proliferative disorder can be treated prophylactically, acutely, or chronically using compounds of the present invention, depending on the nature of the disorder or condition. Preferably, the subject in each of these methods is human.

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. In certain embodiments, the compounds of the present invention are administered intravenously or subcutaneously. Also, the compounds described herein can be administered by inhalation, for example, intranasally. Additionally, the compounds of the present invention can be administered transdermally. In another embodiment, the compounds of the present invention are delivered orally. The compounds can also be delivered rectally, bucally or by insufflation.

Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. A typical dose is about 1 mg to about 1,000 mg per day, such as about 5 mg to about 500 mg per day. In certain embodiments, the dose is about 10 mg to about 300 mg per day, such as about 25 mg to about 250 mg per day.

V. Chemistry

CEP-28122

(1S,2S,3R,4R)-3-[5-chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (CEP-28122) is prepared as described in Example 882 of WO 2008/051547 (Ahmed et al.).

CEP-37440

The synthesis of 2-(5-chloro-2-{(S)-6-[4-(2-hydroxyethyl)-piperazin-1-yl]-1-methoxy-6,7,8,9-tetrahydro-5H-benzocyclohepten-2-ylamino}-pyrimidin-4-ylamino)-N-methyl-benzamide can be carried out according to FIG. 1, following the procedures outlined in Steps 1-8.

Step 1: 5-Methoxy-1-methylene-1,2,3,4-tetrahydro-naphthalene: To a slurry of 5-Methoxy-3,4-dihydro-2H-naphthalen-1-one (25 g, 0.14 mol) and methyltriphenylphosphonium iodide (1.13 eq) in THF (250 mL) at RT was added potassium t-butoxide (1.6 eq) at such a rate as to maintain a temperature no higher than warm to the touch. The reaction was stirred for one hour and concentrated. The reaction was then azeotroped with three volumes of hexane to remove excess t-butanol. Fresh hexane was added the solution was let to stand overnight to effect trituration. The red-brown solid was removed by filtration and the filtrate was washed twice with water and was concentrated. Purification by chromatography on ISCO (330 g SiO2 cartridge: stepwise hexane and then DCM) affords the title compound as a pale yellow oil (24 g, 99%). 1H-NMR (400 MHz, CDCl$_3$) 7.29 (d, J=8.0 Hz, 1H), 7.15 (t, J=8.0 Hz, 1H), 6.76 (d, J=8.0 Hz, 1H), 5.49 (s, 1H), 4.98 (s, 1H), 3.85 (s, 3H), 2.77 (t, J=6.4 Hz, 2H), 2.53-2.50 (m, 2H), 1.93-1.87 (m, 2H).

Step 2: 1-Methoxy-5,7,8,9-tetrahydro-benzocyclohepten-6-one: 5-Methoxy-1-methylene-1,2,3,4-tetrahydro-naphthalene (23.8 g, 0.137 mol) in 150 mL MeOH added in one portion to freshly prepared solution of thallium(III)nitrate trihydrate (1.0 eq) in 300 mL MeOH. Stirred one minute and 400 mL chloroform added. The solution was filtered and the organics partitioned between dichloromethane and water. The organics were dried (MgSO4) and concentrated. Purification by chromatography (ISCO, 330 g silica cartridge; stepwise elution hexane (5 min) then 7 minute gradient to 100% dichloromethane (20 min) affords the title compound as the most polar of the products as a pale yellow oil (26 g, 97%). 1H-NMR (400 MHz, CDCl$_3$) 7.16 (t, J=7.9 Hz, 1H), 7.84 (d, J=8.3 Hz, 1H), 6.79 (d, J=7.5 Hz, 1H), 3.84 (s, 3H), 3.73 (s, 2H), 3.05-3.01 (m, 2H), 2.55 (t, J=7.0 Hz, 2H), 2.01-1.96 (m, 2H). LC/MS (ESI+) m/z=191 (M+H)+

Step 3: 1-Methoxy-2-nitro-5,7,8,9-tetrahydro-benzocyclohepten-6-one: To potassium nitrate in acetonitrile (50 mL) and trifluoroacetic anhydride (100 mL) at 0° C. was added dropwise 1-methoxy-5,7,8,9-tetrahydro-benzocyclohepten-6-one (25 g, 0.131 mol) in 50 mL acetonitrile. The reaction was stirred for 2.5 hours while warming to RT. The reaction was concentrated without heat on a rotary evaporator. MeOH was added and stirred briefly. Reconcentrated and worked-up by partitioning between dichloromethane and sat. sq. sodium bicarbonate solution. The organic layer was separated and dried (Mg2SO4), concentrated and purified by chromatography ISCO (330 g silica cartridge: gradient elution—10 to 50% EA:HEX over 60 minutes) affording two isomers. The title compound was the later eluting (10.7 grams, 34.6% yield). 1H-NMR (400 MHz, CDCl$_3$) 7.70 (d, J=8.3 Hz, 1H), 7.06 (d, J=8.3 Hz, 1H), 3.92 (s, 3H), 3.80 (s, 2H), 3.13-3.09 (m, 2H), 2.60 (t, J=7.0 Hz, 2H), 2.10-2.03 (m, 2H).

Step 4: 2-[4-(1-Methoxy-2-nitro-6,7,8,9-tetrahydro-5H-benzocyclohepten-6-yl)-piperazin-1-yl]-ethanol: 1-Methoxy-2-nitro-5,7,8,9-tetrahydro-benzocyclohepten-6-one (15.09 g, 64.15 mmol) in methylene chloride (870 ml) treated with 2-piperazin-1-yl-ethanol (3 eq) followed by acetic acid (10 eq). The mixture was stirred at 50° C. for 2 hrs and cooled to 0° C. and sodium triacetoxyborohydride (4 eq) was added, then warmed to RT and stirred. After a few hours starting material was still present. Added 0.4 eq further of sodium triacetoxyborohydride, then again after 6 hours. Stirred overnight. Poured into a solution of sat. aq. Sodium bicarbonate and ice and made basic to pH 10 with 1N sodium hydroxide, extracted 2× dichloromethane, dried MgSO4, filtered and concentrated. This material was taken up into ethanol and HCl/ethanol was added. The resulting precipitate was triturated for 2 hours then filtered. The solid was free-based using NaOH followed by sodium bicarbonate and extracted into dichloromethane to give the title compound (19 g, 85% yield). 1H-NMR (400 MHz, CDCl$_3$) 7.56 (d, J=8.2 Hz, 1H), 7.00 (d, J=8.2 Hz, 1H), 3.82 (s, 3H), 3.63-3.06 (m, 2H), 3.29-3.24 (m, 1H), 3.00-2.86 (m, 3H), 2.72-2.67 (m, 2H), 2.60-2.51 (m, 8H), 2.46-2.37 (m, 2H), 2.12-2.07 (m, 2H), 1.87-1.78 (m, 1H), 1.37-1.29 (m, 1H). LC/MS (ESI+) m/z=350 (M+H)+

Step 5: 2-[4-(2-Amino-1-methoxy-6,7,8,9-tetrahydro-5H-benzocyclohepten-6-yl)-piperazin-1-yl]-ethanol. 2-[4-(1-Methoxy-2-nitro-6,7,8,9-tetrahydro-5H-benzocyclohepten-6-yl)-piperazin-1-yl]-ethanol (19.0 g, 54.4 mmol) was split into two batches and dissolved in a total of Ethanol (232 mL). 10% Pd/C (1.74 g, 1.64 mmol) was divided in half and the reaction was hydrogenated for 3-4 hours at 50 psi. Each reaction mixture was filtered through celite to remove Pd. The filtrates were combined and then concentrated and the title compound isolated as a foamy solid (17.25 g, 99% yield). 1H-NMR (400 MHz, CDCl$_3$) 6.76 (d, J=7.9 Hz, 1H), 6.53 (d, J=7.9 Hz, 1H), 3.72 (broad s, 3H), 3.71 (s, 3H), 3.64 (t, J=5.4 Hz, 2H), 3.26-3.20 (m, 1H), 2.84-2.72 (m, 5H), 2.62-2.56 (m, 8H), 2.42-2.35 (m, 2H), 2.40-2.37 (m, 1H), 1.81-1.74 (m, 1H), 1.70 (broad s, 1H), 1.41-1.33 (m, 1H). LC/MS (ESI+) m/z=320 (M+H)+

Step 6: 2-[4-((S)-2-Amino-1-methoxy-6,7,8,9-tetrahydro-5H-benzocyclohepten-6-yl)-piperazin-1-yl]-ethanol: 34 grams of racemic 2-[4-(2-Amino-1-methoxy-6,7,8,9-tetrahydro-5H-benzocyclohepten-6-yl)-piperazin-1-yl]-ethanol were separated using SFC (supercritical fluid $CO_2$) chromatography using a Chiralcel OJ-H (3×15 cm) 808041 column with 15% methanol (0.2% DEA)/CO2, 100 bar eluent at 80 mL/min flow rate monitoring the wavelength of 220 nm with an injection volume: 0.5 mL, 20 mg/mL ethanol. 16.9 grams of the (R)-enantiomer and 17 grams of the titled compound were isolated with a chemical purity >99% and an enantiomeric excess (ee)>99% (measured using a Chiralcel OJ-H analytical column) NMR and mass were equivalent to the racemic material. The absolute configuration of the first eluting isomer was unambiguously assigned as the (R)-configuration via small-molecule X-ray using anomalous dispersion of the bis-p-bromobenzyl derivative: 4-bromo-benzoic acid 2-{4-[(R)-2-(4-bromo-benzoylamino)-1-methoxy-6,7,8,9-tetrahydro-5H-benzocyclohepten-6-yl]-piperazin-1-yl}-ethyl ester. Thus, the second eluting enantiomer was determined to be (S)-configuration.

Step 7: 2-(2,5-Dichloro-pyrimidin-4-ylamino)-N-methyl-benzamide: 2-Amino-N-methyl-benzamide (24.4 g, 0.16 mol) in DMF (0.5 L) was added 2,4,5-Trichloro-pyrimidine (39 g, 1.3 eq) and Potassium carbonate (1.3 eq). Stirred under argon at 75° C. for 5 hrs and then at RT overnight. Poured into 1 L water and precipitate isolated by filtration and washed 1:1 acetonitrile:water followed by drying in air stream and under vacuum to afford the title compound as a yellow solid (38 g, 78% yield). 11.70 (s, 1H), 8.74 (d, J=8.2 Hz, 1H), 8.24 (s, 1H), 7.59 (d, J=8.4 Hz, 1H), 7.53 (d, J=8.8 Hz, 1H), 7.16 (t, J=8.4 Hz, 1H), 6.28 (s, 1H), 3.06 (d, J=4.7 Hz, 3H).

Step 8: 2-(5-Chloro-2-{(S)-6-[4-(2-hydroxy-ethyl)-piperazin-1-yl]-1-methoxy-6,7,8,9-tetrahydro-5H-benzocyclohepten-2-ylamino}-pyrimidin-4-ylamino)-N-methyl-benzamide: To a sealed vessel 2-[4-((S)-2-Amino-1-methoxy-6,7,8,9-tetrahydro-5H-benzocyclohepten-6-yl)-piperazin-1-yl]-ethano (2.69 g, 8.41 mmol) and 2-(2,5-Dichloro-pyrimidin-4-ylamino)-N-methyl-benzamide (2.00 g, 6.73 mmol) were combined in 1-methoxy-2-propanol (120 mL, 1200 mmol) followed by the addition of Methanesulfonic acid (2.44 mL, 37.7 mmol). The reaction was then heated at 90° C. for 18 hours. The reaction mixture was added to a separatory funnel and diluted with sat. bicarb until a cloudy ppt formed. This was extracted with dichloromethane 3×. The organic layer was then washed with brine, dried over MgSO4, filtered and concentrated. The residue was pumped dry then chromatographed on ISCO flash column. It was injected in dichloromethane onto a normal phase column and eluted on a gradient of 0-10% (dichloromethane:10% NH4OH in MeOH). The desired product eluted around 9-10% and the 10% gradient was held until product eluted completely. Mixed fractions concentrated and were chromatographed on the Gilson reverse-phase HPLC gradient elution 0-40% $CH_3CN$. Chromatogrpahy was repeated using normal phase silica and reverse phase HPLC to effect further purification as desired. Following neutralization and concentration of all the material, the resulting solid was obtained by taking the foam up into EtOAc and concentrating to dryness several times to give the title compound (1.1 g, 28%). 11.02 (s, 1H), 8.69 (d, J=8.9 Hz, 1H), 8.13 (s, 1H), 8.08 (d, J=8.4 Hz, 1H), 7.59-7.50 (m, 2H), 7.41 (s, 1H), 7.13 (t, J=7.4 Hz, 1H), 6.91 (d, J=8.1 Hz, 1H), 6.21 (s, 1H), 3.74 (m, 3H), 3.66-3.63 (m, 2H), 3.29-3.23 (m, 1H), 3.06 (d, J=4.3 Hz, 3H), 2.92-2.72 (m, 5H), 2.66-2.55 (m, 8H), 2.48-2.39 (m, 2H), 2.16-2.10 (m, 2H), 1.87-1.77 (m, 1H), 1.42-1.32 (m, 1H). LC/MS (ESI+) m/z=580 (M+H)+

CEP-37440 Amorphous HCl Salt 2-(5-Chloro-2-{6-[4-(2-hydroxy-ethyl)-piperazin-1-yl]-1-methoxy-6,7,8,9-tetrahydro-5H-benzocyclohepten-2-ylamino}-pyrimidin-4-ylamino)-N-methyl-benzamide hydrochloride: 2-(5-Chloro-2-{6-[4-(2-hydroxy-ethyl)-piperazin-1-yl]-1-methoxy-6,7,8,9-tetrahydro-5H-benzocyclohepten-2-ylamino}-pyrimidin-4-ylamino)-N-methyl-benzamide (4.90 g, 8.45 mmol) and 2.5 M of HCl in ethanol (13.5 mL, 33.8 mmol) were heated until they dissolved in ethanol (164 mL). The reaction was concentrated two times from ethanol, then warmed in a small amount of ethanol until completely dissolved. This solution was allowed to cool slowly with a stirring (<100 rpm). A solid precipitate formed quickly before the solution had cooled. This mixture was allowed to stir until ambient temperature was achieved and then filtered. The solid was washed with ethanol followed by ether then directly pumped dry under high vac to give 2-(5-chloro-2-{6-[4-(2-hydroxy-ethyl)-piperazin-1-yl]-1-methoxy-6,7,8,9-tetrahydro-5H-benzocyclohepten-2-ylamino}- pyrimidin-4-ylamino)-N-methyl-benzamide hydrochloride (5.3 grams, quantitative yield). 1H-NMR (MeOD, 400 MHz) δ 8.55 (s, 1H), 8.17 (s, 1H), 7.80 (d, J=7.7 Hz, 1H), 7.55 (t, J=6.8 Hz, 1H), 7.46 (broad s, 1H), 7.36 (t, J=7.2 Hz, 1H), 7.23 (d, J=8.5 Hz, 1H), 4.00-3.95 (m, 4H), 3.83-3.72 (m, 5H), 3.73 (s, 3H), 3.65-3.59 (m, 2H), 3.47-3.38 (m, 5H), 2.95 (s, 3H), 2.72-2.65 (m, 1H), 2.44-2.38 (m, 1H), 2.29-2.28 (m, 1H), 2.19-2.12 (m, 1H), 1.59-1.49 (m, 1H). LC/MS (ESI+) m/z=580 (M+H)+.

CEP-37440 Salt Screening

Salt screening experiments were performed (a) in methanol using 27 different acids (acetic acid, ascorbic acid, benzenesulfonic acid, citric acid, D—glucuronic acid, DL glutamic acid, DL—lactic acid, ethane-1,2-disulfonic acid, ethanesulfonic acid, fumaric acid, glycolic acid, hippuric acid, hydrobromic acid (48% aq), hydrochloric acid (2.5M, EtOH), L—aspartic acid, L—tartaric acid, L—pyroglutamic acid, lactobionic acid, maleic acid, malic acid, malonic acid, naphthalene-2-sulfonic acid, ortho phosphoric acid, p-toluenesulfonic acid monohydrate, propionic acid, succinic acid, and sulfuric acid), (b) in dichloromethane and tetrahydrofuran using 9 different acids (benzenesulfonic acid, ethane-1, 2-disulfonic acid, ethanesulfonic acid, hydrobromic acid (48% aq), naphthalene-2-sulfonic acid, o-phosphoric acid (85%), sulfuric acid, p-toluenesulfonic acid, and hydrochloric acid (ethanol)), and (c) in chloroform, acetone, ethyl acetate, and 1-propanol using benzenesulfonic acid, hydrobromic acid (48% aq), o-phosphoric acid, sulfuric acid, p-toluenesulfonic acid, and hydrochloric acid (ethanol)). Although many of the experiments provided salt forms, only a few of the experiments resulted in crystalline salts, and only two salt forms were crystalline, stable, and reproducible: a tri-benzenesulfonate form and a trihydrochloride dihydrate form. From a pharmaceutical perspective the trihydrochloride dihydrate is favored over the tri-benzenesulfonate because HCl is a Class 1 acid addition salt that is generally recognized as safe (GRAS), whereas benzenesulfonic acid is a Class 2 acid addition salt that is not GRAS (see Stahl, H. P. & Wermuth, C. G., Editors, 2002 Handbook of Pharmaceutical salts; Properties, Selection, and Use. Vwerlag HelveticaChimica Acta and Wiley-VCH). In addition to being less toxic, HCl has a lower molecular weight than benezensulfonic acid, which provides a higher API/acid ratio and a lower effective dose.

Powder X-ray diffraction patterns were recorded on a PANalytical X Pert Pro diffractometer equipped with an X'celerator detector using CuK$_\alpha$ radiation at 45 kV and 40 mA. K$_{\alpha1}$ radiation was obtained with a highly oriented crystal (Ge111) incident beam monochromator. A 10 mm beam mask, and fixed (¼°) divergence and anti-scatter (⅛°) slits were inserted on the incident beam side. A fixed 5 mm receiving slit and a 0.04 radian Soller block were inserted on the diffracted beam side. The X-ray powder pattern scan was collected from ca. 2 to 40° 2θ with a 0.0080° step size and 96.06 sec counting time which resulted in a scan rate of approximately 0.5°/min. The sample was spread on silicon zero background (ZBG) plate for the measurement. The sample was rotated using a PANalytical PW3064 Spinner (15 revolutions/min.). Measurement of the Si reference standard before the data collection resulted in values for 2θ and intensity that were well within the tolerances of 28.44<2θ<28.50 and significantly greater than the minimum peak height of 150 cps.

CEP-37440 Tribenzenesulfonate

CEP-37440 free base (500 mg, 0.862 mmoles) was dissolved in 6 mL of tetrahydrofuran by stirring at room temperature for 5 minutes. This solution was added one mL at a time to benzenesulfonic acid (545.6 mg, 3.45 mmoles) in a glass 20 mL scintillation vial (16×60 mm). The sample was mixed using a stirring bar during the addition (at room temperature). An oil plus a solid was noted when all of the CEP-37440 solution was added. The sample was stirred at 5-7° C. for 19 hours on a HEL Polyblock™ unit. The solid was isolated by suction filtration. The solid was dried at 50° C. under house vacuum for 5 hours to give 835 mg (80% recovery) of slightly yellow solid. The HPLC purity, assay, and compound color were improved by suspending 616 mg in 1.5 mL of water and stirring the resulting slurry for 30 minutes at room temperature. The solid was isolated by suction filtration and the solid on the filter pad was washed with 1 mL of water. The white solid was dried at 50° C. under house vacuum for 68 hours to yield 406 mg (67% recovery). The tribenzenesulfonate salt has a water solubility of about 20-33 mg/mL.

Figure 2:
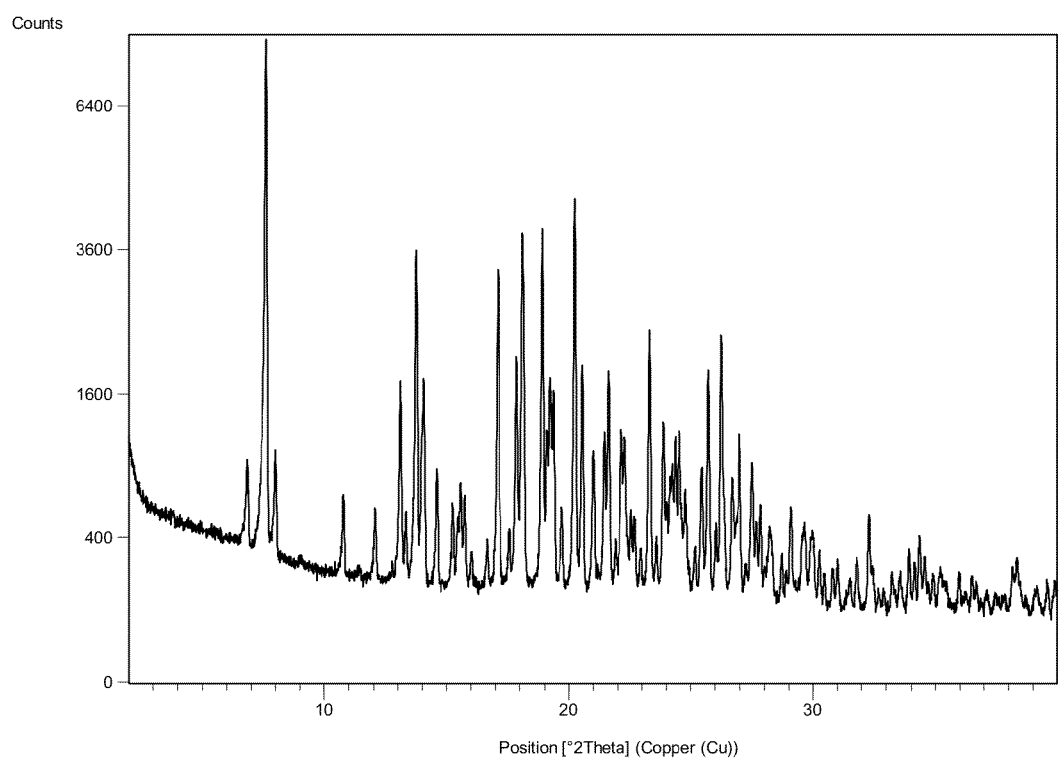
FIG. 2 depicts an XRPD pattern of a crystalline CEP-37440 tribenzenesulfonate salt.

The X-ray diffraction data characteristic of the crystalline tribenzenesulfonate salt is shown in Table 1 and FIG. 2.

TABLE 1

Higher Relative Intensities with Two Theta Positions and d-Spacings for the XRPD Pattern of the CEP-37440 tribenzenesulfonate salt

| No. | Pos. [2θ.] | d-spacing [Å] | Rel. Int. [%] |
|---|---|---|---|
| 1 | 6.85 | 12.897 | 8 |
| 2 | 7.62 | 11.593 | 100 |
| 3 | 8.01 | 11.031 | 9 |
| 4 | 10.77 | 8.209 | 6 |
| 5 | 12.07 | 7.324 | 5 |
| 6 | 13.11 | 6.747 | 20 |
| 7 | 13.34 | 6.630 | 5 |
| 8 | 13.76 | 6.430 | 44 |
| 9 | 14.05 | 6.296 | 21 |
| 10 | 14.60 | 6.061 | 9 |
| 11 | 15.25 | 5.805 | 6 |
| 12 | 15.47 | 5.724 | 5 |
| 13 | 15.57 | 5.686 | 8 |
| 14 | 15.74 | 5.625 | 6 |
| 15 | 16.02 | 5.528 | 2 |
| 16 | 16.66 | 5.317 | 3 |
| 17 | 17.10 | 5.181 | 40 |
| 18 | 17.59 | 5.038 | 4 |
| 19 | 17.86 | 4.962 | 24 |
| 20 | 18.10 | 4.898 | 47 |

The highest peak (intensity 100%) is set in bold letters.

CEP-37440 Trihydrochloride Dihydrate

In a 20 mL scintillation vial containing 200 mg of CEP-37440 free base was added n-butyl alcohol (5 mL) at room temperature. After stirring for 5 minutes, the free base was in solution. HCl (2.5 M in EtOH, 0.435 mL, 3.15 eq) was then added resulting in the immediate precipitation of white solids (amorphous HCl salt). The resulting slurry was heated to 85° C. over 20 minutes. (Note: at approximately 60° C., no solids remained out of solution.) Stirring the solution between 80 and 85° C. resulted in self nucleation after 30 minutes which resulted in further precipitation of white solids. After stirring the reaction for a total of 2 hours, the resulting slurry was cooled to 5° C. over 1 hour. The 0-5° C. slurry was stirred for an additional hour then filtered, washing with minimal cold n-butyl alcohol. The solids were then dried at 55° C. overnight. Upon standing to RH 30-70% air, 208 mg of CEP-37440-3HCl-2H$_2$O were obtained.

Figure 3:
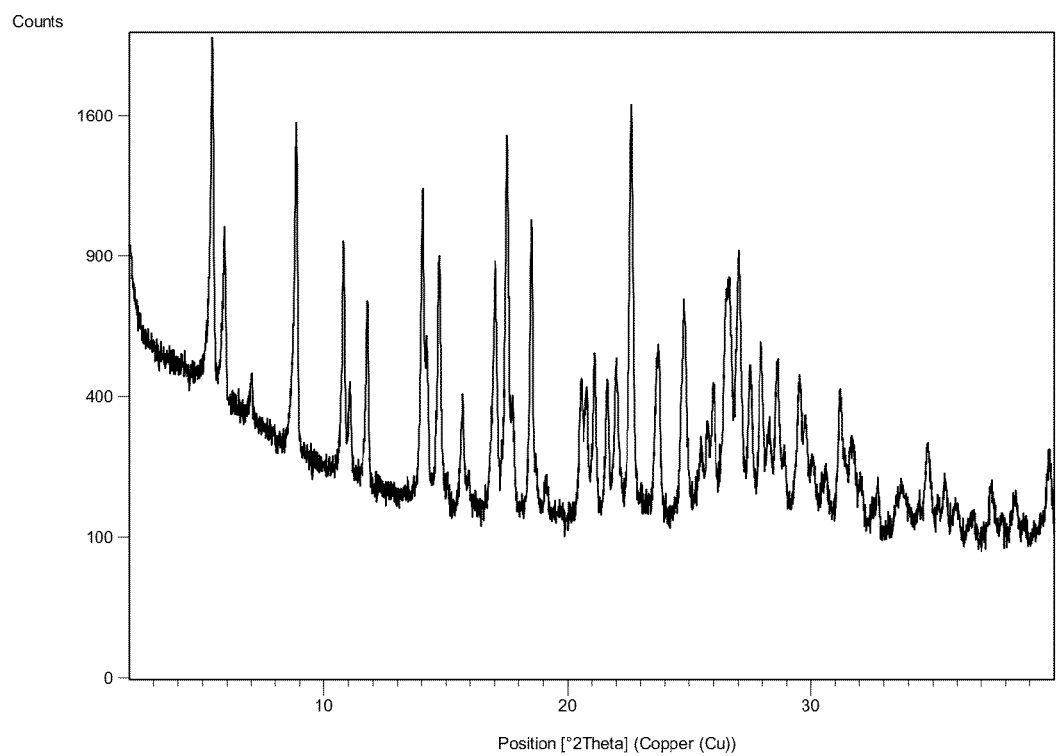
FIG. 3 depicts an XRPD pattern of a crystalline CEP-37440 trihydrochloride dihydrate salt.

The X-ray diffraction pattern characteristic of the crystalline trihydrochloride dihydrate salt is shown in Table 2 and FIG. 3. The salt is stable at 30-80% relative humidity, but reversibly converts to a trihydrochloride monohydrate form below 30% RH and irreversibly converts to a highly hydrated amorphous form above 80% RH.

TABLE 2

Higher Relative Intensities with Two Theta Positions and d-Spacings for the XRPD Pattern of the CEP-37440 trihydrochloride dihydrate salt

| No. | Pos. [2θ.] | d-spacing [Å] | Rel. Int. [%] |
|---|---|---|---|
| 1 | 5.42 | 16.306 | 100 |
| 2 | 5.91 | 14.940 | 39 |
| 3 | 7.02 | 12.575 | 8 |
| 4 | 8.86 | 9.967 | 77 |
| 5 | 10.80 | 8.184 | 46 |
| 6 | 11.06 | 7.995 | 14 |
| 7 | 11.79 | 7.498 | 33 |
| 8 | 14.06 | 6.292 | 64 |
| 9 | 14.22 | 6.223 | 26 |
| 10 | 14.72 | 6.014 | 45 |
| 11 | 15.70 | 5.641 | 15 |
| 12 | 17.02 | 5.204 | 44 |
| 13 | 17.52 | 5.059 | 83 |
| 14 | 17.76 | 4.990 | 14 |
| 15 | 18.51 | 4.789 | 56 |
| 16 | 19.13 | 4.635 | 3 |
| 17 | 20.56 | 4.316 | 20 |
| 18 | 20.79 | 4.269 | 17 |
| 19 | 21.12 | 4.204 | 24 |
| 20 | 21.66 | 4.099 | 17 |

The highest peak (intensity 100%) is set in bold letters.

VI. Biology 13-week Oral Toxicity and Toxicokinetic Study of CEP-28122 in Sprague-Dawly Rats, Including a 4-week Recovery Period Three treatment groups of 20 rats/sex were administered CEP-28122 at respective dose levels of 30, 75, and 150 mg free base/kg/day (administered as the mono-methanesulfonic acid, mono-HCl salt form). One additional group of 20 animals/sex served as the control and received the vehicle, distilled water. The drug or vehicle was administered to all groups via oral gavage, once a day for 91 consecutive days, at a dose volume of 10 mL/kg/dose. Following the dosing period, five animals/sex/group were maintained for a 4-week recovery period. Additionally, one group of three animals/sex and three groups of nine animals/sex/group served as toxicokinetic (TK) animals and received the vehicle or drug in the same manner and at the same dose levels as the main study groups.

Observations for morbidity, mortality, injury, and the availability of food and water were conducted at least twice daily for all animals. Clinical observations were conducted on main study animals weekly. Body weights were measured and recorded for all animals prior to initiation of dosing (week -1) and weekly during the study. Food consumption was measured and recorded for main study animals weekly. Ophthalmoscopic examinations were conducted on main study animals pretest and prior to the terminal and recovery necropsies. Blood samples for designated clinical pathology evaluations were collected from main study animals at the end of week 4 and at the terminal and recovery necropsies. Urine samples for urinalysis evaluations were collected from main study animals prior to the terminal and recovery necropsies. Blood samples for determination of the plasma concentrations of the drug were collected from designated TK animals at designated time points on day 1, week 4, and week 13. After the final blood collection, the TK animals were euthanized and the carcasses were discarded. At the end of the terminal and recovery periods, necropsy examinations were performed, organ weights were recorded, and selected tissues were microscopically examined.

13-week Oral Toxicity and Toxicokinetic Study of CEP-28122 in Cynomolgus Monkeys with a 6-week Recovery Period CEP-28122 solutions were prepared weekly by dissolution of a CEP-28122 mono-methanesulfonic acid, mono-HCl salt in sterile water for injection (SWFI) to achieve the desired dose concentration levels.

Forty experimentally naive cynomolgus monkeys (20 males and 20 females), 2.5 to 4.4 years of age for the males and 2.5 to 4.0 years of age for the females, and weighing 2.1 to 3.3 kg for the males and 2.0 to 3.1 kg for the females at the outset (Day -1) of the study, were assigned to one of three dose groups and a vehicle control group. Five animals/sex were assigned to each dose group and were given daily oral doses of 0 (vehicle), 20, 40 or 80 mg/kg for up to 91 days. Due to the occurrence of seizures in several animals given 80 mg/kg/day during the first two weeks of dosing, the high dose was lowered to 60 mg/kg/day. Three animals/sex/group were scheduled for termination at the end of the dosing period (Day 92) and two animals/sex/group were assigned to a 6-week non-dosing recovery phase and were terminated on Day 134.

The animals were evaluated for changes in clinical signs (cage side observations and food consumption [twice daily], and post dose observations [1-2 hours post dose on each dosing day]), body weight (Weeks -2 and -1, and weekly thereafter starting on Day 7, and prior to necropsy), electrocardiograms, ophthalmic examinations, and blood pressure measurements (prestudy and in Weeks 1, 4, and 13), echocardiographic measurements (Week 11), clinical pathology indices, including serum chemistry, hematology, and coagulation (within one week prior to the initiation of dosing and near the end of Weeks 1, 4, 10, and 13; and from remaining animals near the end of the recovery period; and troponin I (prestudy; prior to dose and 2, 4, and 24 hours following a dose in Weeks 1, 4, and 13, and at a single time point near the end of the recovery phase). Urine samples for urinalysis only were obtained by bladder puncture during necropsy. Urine samples for urinalysis and urine chemistry analysis were also obtained by drainage from special stainless-steel cage pans in Weeks -1, 1, 4, and 13, and from the remaining animals near the end of the recovery period.

Blood samples were collected for toxicokinetic analysis at various time points on Day 1 and during Weeks 4 and 13. Twenty-one animals (3/sex/Group 1, 2 males/3 females/Group 2, 3 males/2 females/Group 3 and 2 males/3 females/Group 4) were euthanized one day after the last dose. The remaining 14 animals (2/sex each from Groups 1 and 2, 1 male/2 females/Group 3, and 2 males/1 female/Group 4) were continued on study without further dosing, and euthanized approximately 6 weeks after the last dose. At termination, a full necropsy was conducted on all animals, and tissues were collected, preserved, processed, and examined microscopically by a Veterinary Pathologist certified by the American College of Veterinary Pathologists.

4-week Oral Toxicity and Toxicokinetic Study of CEP-28122 in Cynomolgus Monkeys with a 4-week Recovery Period CEP-28122 (mono-methanesulfonate, mono-HCl salt) was administered via oral gavage to groups of cynomolgus monkeys (5/sex/group) at dose levels of 0 (vehicle control), 3, 10, 20 or 40 mg/kg/day. Following the 4-week treatment period, 3 animals/sex/group were terminated and 2 animals/sex/group entered a 4-week treatment-free recovery period.

The following parameters and end points were evaluated in this study: clinical signs (mortality/moribundity checks, cage side observations and food consumption, and postdose observations), body weights, veterinary physical examinations, lung evaluations, ophthalmology, electrocardiography, blood pressure and heart rate measurements, clinical pathology parameters (hematology, coagulation, clinical chemistry, urinalysis, urine chemistry, and troponin I analysis), toxicokinetic parameters, gross necropsy findings, organ weights, and histopathologic examinations.

4-week Oral Toxicity and Toxicokinetic Study of CEP-37440 in Sprague-Dawley Rats with a 4-week Recovery Period Male and female rats (15/sex/group) were assigned to 4-treated groups, and a vehicle control group (pH-adjusted reverse osmosis water), and the CEP-37440 was administered as the trihydrochloride dihydrate salt as indicated in the following table. Animals were dosed via oral gavage.

| Group[a] | Subgroup[b] | No. of Animals | | Dose Level[c,d] (mg/kg/day) |
|---|---|---|---|---|
| | | Male | Female | |
| 1 (Control) | 1 (Toxicity) | 15 | 15 | 0 |
| | 2 (Toxicokinetic) | 3 | 3 | 0 |
| 2 (Low) | 1 (Toxicity) | 15 | 15 | 1 |
| | 2 (Toxicokinetic) | 9 | 9 | 1 |
| 3 (Mid) | 1 (Toxicity) | 15 | 15 | 3 |
| | 2 (Toxicokinetic) | 9 | 9 | 3 |
| 4 (Mid-High) | 1 (Toxicity) | 15 | 15 | 10 |
| | 2 (Toxicokinetic) | 9 | 9 | 10 |
| 5 (High) | 1 (Toxicity) | 15 | 15 | 30 |
| | 2 (Toxicokinetic) | 9 | 9 | 30 |

[a]Group 1 received vehicle control (pH-adjusted RO water) only.
[b]Toxicity animals designated for recovery sacrifice (up to five animals/sex in Groups 1, 2, 3, 4, and 5) underwent 4 weeks of recovery following administration of the last dose.
[c]Doses expressed as free base.
[d]The dose volume was 10 mL/kg.

Assessment of toxicity was based on mortality, clinical observations, body weights, body weight changes, food consumption, ophthalmic examinations, and clinical and anatomic pathology. Blood samples were collected for toxicokinetic evaluations.

4-week Oral Toxicity and Toxicokinetic Study of CEP-37440 in Cynomolgus Monkeys with a 4-week Recovery Period Male and female cynomolgus monkeys (*Macaca fascicularis*) were assigned to 4 groups (3-treated and a vehicle control group) consisting of 5 monkeys/sex/group. Dose levels evaluated in this study were 0 (pH-adjusted reverse osmosis water), 2.5, 7.5, and 20 mg/kg/day. The dosing volume was 5 mL/kg. CEP-37440 was administered as the trihydrochloride dihydrate salt form. After completion of the dosing phase, 3 monkeys/sex/group were euthanized and 2 monkeys/sex/group continued on a treatment-free recovery phase for an additional 4 weeks.

Anti-tumor Efficacy Studies—General Protocol

Tumor-bearing mice were randomized into different treatment groups (8-10 mice/group) and were administered orally with either vehicle (PEG-400) or test compound formulated in PEG-400 at indicated doses (expressed as mg/kg equivalents of free base) and with indicated dosing frequency (bid or qid), with 100 µL per dosing volume. The length (L) and width (W) of each tumor was measured with a vernier caliper and the mouse body weight was determined every 2-3 days. The tumor volumes were then calculated with the formula of $0.5236*L*W*(L+W)/2$. Statistical analyses of tumor volumes and mouse body weight were carried out using the Mann-Whitney Rank Sum Test. Plasma and tumor samples were obtained at 2 hours post final dose at each dose level, and the compound levels in plasma and tumor lysates were measured by LCMS/MS.

Anti-Tumor Efficacy in NPM-ALK Positive Sup-M2 and Karpas-299 ALCL Tumor Xenograft Models in Mice CEP-37440 is administered po in PEG400 qd or bid to mice containing NPM-ALK positive Sup-M2 ALCL tumor xenografts for 12 days. The anti-tumor efficacy of CEP-37440 (amorphous HCl salt) in a second, more resistant NPM-ALK-positive ALCL (Karpas-299) tumor xenograft model in Scid mouse was also evaluated.

Anti-Tumor Activity in EML4-ALK Positive (NCI-H2228 and NCI-H3122) NSCLC Tumor Xenografts in Mice with Oral Dosing Human lung cancer cell lines, NCI-H2228 and NCI-H1650 (ATCC, Manassas, Va.), and NCI-H3122 (kindly provided by Dr. Giorgio Inghirami, Univ. of Torino, Italy), were grown in RPMI-1640 medium supplemented with 10% fetal bovine serum (FBS, Cat#SH3007003, Hyclone, Logan, Utah). NCI-H2228 cells harbor EML4-ALK variant 3a/b and NCI-H3122 cells contain EML4-ALK variant 1, determined by fluorescence in situ hybridization and reverse-transcription-PCRas previously reported (Koivunen J P, Mermel C, Zejnullahu K, Murphy C, Lifshits E, Holmes A J, et al. EML4-ALK fusion gene and efficacy of an ALK kinase inhibitor in lung cancer. Clin Cancer Res 2008, 14:4275-8).

Generation of EML4-ALK-positive and EML4-ALK-negative NSCLC Subcutaneous Tumor Xenografts in Scid Mice Female Scid/Beige mice (6-8 weeks, Taconic, Hudson, N.Y.) were maintained 5/cage in microisolator units on a standard laboratory diet (Teklad Labchow, Harlan Teklad, Madison, Wis.). Animals were housed under humidity- and temperature controlled conditions and the light/dark cycle was set at 12-hour intervals. Mice were quarantined at least 1 week prior to experimental manipulation. All animal studies were conducted under protocol (#03-023) approved by the Institutional Animal Care and Use Committee (IACUC) of Cephalon, Inc. Briefly, EML4-ALK-positive and -negative NSCLC cells were collected and resuspended in RPMI-1640 medium at density of $5\times10^7$/mL. An aliquot (100 µL) of the cell suspension ($5\times10^6$ cells) was inoculated subcutaneously to the left flank of each mouse with a 23 g needle (23G1, Cat#305145, Becton Dickinson, Franklin, N.J.). The mice were monitored until the tumor xenograft volumes reached 200-500 mm3.

The tumor bearing mice were randomized into different treatment groups (8-10 mice/group) and were administered either vehicle (PEG-400) or CEP-37440 amorphous HCl salt formulated in PEG-400 at indicated doses, bid, with 100 µL per dosing volume. The length (L) and width (W) of each tumor were measured with vernier calipers and the mouse body weight was determined every two to three days. Tumor volumes were calculated with the formula of $0.5236*L*W*(L+W)/2$. Percent tumor growth inhibition (% TGI) was calculated as follows: (tumor volume of the control group at end of treatment−tumor volume of the treated group at the end of treatment)/tumor volume of the control group at the end of treatment. Partial tumor regression (PR) was defined as the tumor volume of the treated group at the end of treatment being less than that of the treated group at the start of treatment. Complete tumor regression (CR) was defined as the tumor volume of the treated group at the end of treatment being less than 5% of the tumor volume of the treated group as the start of treatment. Statistical analyses of tumor volumes and mouse body weights were carried out with the Mann-Whitney Rank Sum Test. Plasma and tumor samples were obtained at 2 hours post final dose at each dose level, and the compound levels in plasma and tumor lysates were measured by LC-MS/MS Anti-Tumor Efficacy Studies in Human Tumor Xenografts of Hormone-independent Prostate Carcinoma, NSCL Carcinoma and HNSC Carcinoma The human prostate carcinoma cell lines, CWR22 and PC3, and human head and neck squamous cell carcinoma cell line Detroit 562 were obtained from American Tissue Culture Collection (ATCC, Manassas, Va.). CWR22 cells were cultured in RPMI (ATCC, Cat#30-2001,) supplemented with 10% fetal bovine serum (FBS, Cat#SH3007003, Hyclone Laboratory Inc, Logan, Utah), PC3 were cultured in F12 medium (ATCC, Cat#30-2004,) supplemented with 10% FBS, and Detroit 562 were cultured in EMEM (ATCC, Cat#30-2003,) supplemented with 10% FBS. Human non-small cell lung cancer cell line HCC-827 and human breast cancer cell line BT474 were also purchased from the ATCC (Manassas, Va.) and cultured in RPMI (Cat#10-040, Mediatech Inc, Manassas, Va.) with 10% FBS. The rabbit phospho-FAK (Tyr397) (Cat#3283) and FAK antibodies (Cat#3285) were purchased from Cell Signaling Technology (Beverly, Mass.).

Generation of Subcutaneous Human Tumor Xenografts in SCID/Beige or Nu/Nu Mice Female SCID/Beige (6-8 weeks, Taconic, Hudson, N.Y.) or Nu/Nu mice (6-8 weeks, Charles River Laboratory, Wilmington, Mass.) were maintained 5/cage in microisolator units on a standard laboratory diet (Teklad Labchow, Harlan Teklad, Madison, Wis.). Animals were housed under humidity- and temperature-controlled conditions and the light/dark cycle was set at 12-hour intervals. Mice were quarantined at least 1 week prior to experimental manipulation. Experiments were approved (Protocol 03-023) by the Institutional Animal Care and Use Committee of Cephalon, Inc. Briefly, the cells were collected and resuspended in RPMI medium at density of $5 \times 10^7$/mL and an aliquot (100 µL) of the cell suspension ($4 \times 10^6$ or $5 \times 10^6$ cells) was inoculated subcutaneously to the left flank of each mouse with a 23 g needle (23G1, Cat#305145, Becton Dickinson, Franklin, N.J.). The mice were then monitored daily.

The tumor-bearing mice were randomized into different treatment groups (8-10 mice/group) and were administered orally with either vehicle (PEG-400) or CEP-37440 formulated in PEG-400 at indicated doses (expressed as mg/kg equivalents of free base) and with indicated dosing frequency, with 100 µL per dosing volume. The length (L) and width (W) of each tumor was measured with a vernier caliper and the mouse body weight was determined every 2-3 days. The tumor volumes were then calculated with the formula of $0.5236*L*W*(L+W)/2$. Statistical analyses of tumor volumes and mouse body weight were carried out using the Mann-Whitney Rank Sum Test. Plasma and tumor samples were obtained at 2 hours post final dose at each dose level, and the compound levels in plasma and tumor lysates were measured by LC-MS/MS. The TGI values were calculated at the end of study by comparing the tumor volumes (TV) of each CEP-37440-treatment group with those of vehicle-treated group with the following formula: [1−(the last day TV of compound-treated group/the last day TV of vehicle treated group)]*100.

VII. Results

Biological data for CEP-37440 and CEP-28122 are summarized in Table 3 and presented and discussed below.

TABLE 3

Summary of data for CEP-37440 and CEP-28122

| Activity | CEP-37440 | CEP-28122 |
|---|---|---|
| ALK enzymatic $IC_{50}$ (nM) | 3.5 | 3 |
| ALK cellular $IC_{50}$ (nM) | 40 | 30 |
| ALK cellular $IC_{50}$ in 75% murine plasma (nM) | 200 | 300 |
| ALK cellular $IC_{50}$ in 75% human plasma (nM) | 120 | 300 |
| FAK enzymatic $IC_{50}$ (nM) | 2.3 | 29.5 |
| FAK cellular $IC_{50}$ (nM) | 82 | 944 |
| Enzymatic IR $IC_{50}$ (nM) | 66 | 996 |
| Enzymatic IR/ALK $IC_{50}$ ratio | 19 | 332 |
| Cellular IR $IC_{50}$ (nM) | 2000 | >10,000 |
| Cellular IR/ALK $IC_{50}$ ratio | 50 | >333 |
| Kinase selectivity - 442 kinases (Ambit KINOMEscan profiling @ 1 µM) | S(80): 0.131; S(90): 0.084; S(99): 0.016 | S(80): 0.172; S(90): 0.125; S(99): 0.016 |
| Receptor selectivity (Cerep) (Ki, µM) | Histamine H2 = 5.2; Muscarinic: M1 = 2.46, M2 = 2.0, M3 = 3.5, M4 = 0.46; Neurokinin: NK1 = 1.2; Serotonin: 5-HT1B = 3.3; DA transporter = 2.1 | Adrenergic $\alpha_{1B}$ (R), 2.2; Adrenergic $\alpha_{1D}$ (H), 1.1 |
| hERG patch clamp ($IC_{50}$, µM) | >10 | >10 |
| Equilibrium solubility at pH 2/pH 7.4 (mg/mL) | >1/0.28 | >3/0.013 |
| cLog $D_{7.4}$ | 2.95 | 3.9 |
| In vitro metabolic stability ($t_{1/2}$, min) | >40 (M), >40 (R), 21 (Mo), >40 (H) | 13.2 (M), 6.7 (R), 19.9 (D), <5 (Mo), 10.3 (H) |
| CYP inhibition ($IC_{50}$, µM) | 1A2: >30; 2C9: >30; 2C19: >20; 2D6: >30; 3A4: 5 | 1A2: >30; 2C9: 1.3; 2C19: 6.8; 2D6: 17.3; 3A4: 1.1 |
| CYP3A4 induction in vitro (fold) | 1.5 @ 10 µM | 0.95 @ 0.3 µM; 1.3 @ 3.0 µM; 2.0 @ 10 µM |
| Caco-2 $P_{app} \times 10^{-6}$ cm/s (PDR) | 1.26 (PDR: 4.7) | 12.6 (PDR: 3.6) |
| Protein binding (% bound) | 85 (M), 94 (D), 95 (H) | 95 (M), 96 (D), 99.2 (H) |
| Rat bioavailability | >42% | 25% |

TABLE 3-continued

Summary of data for CEP-37440 and CEP-28122

| Activity | CEP-37440 | CEP-28122 |
|---|---|---|
| Mouse bioavailability | 102% (CD-1), 99% (Scid) | 51% (CD-1), 71% (Scid) |
| Monkey bioavailability | 50%@10 mg/kg, 74%@30 mg/kg | 16%@10 mg/kg, 37%@30 mg/kg | metabolic stability/protein binding: (M) mouse, (R) rat, (Mo) monkey, (H) human, (D) dog
mouse and monkey bioavailability experiments for CEP-37440 were performed with the CEP-37440 amorphous HCl salt These data indicate that both CEP-37440 and CEP-28122 are potent ALK inhibitors. However, CEP-37440 is advantageous in comparison to CEP-28122 in that CEP-37440 is a far more potent FAK inhibitor, has reduced protein binding and increased activity in human plasma, increased intrinsic solubility (facilitates absorption), reduced lipophilicity (higher lipophilicity has been associated with increased toxicity), increased metabolic stability (facilitates higher blood concentration at lower doses, which reduces xenobiotic burden on the body–less exposure to drug and metabolites and less pressure on the metabolic system, e.g., liver), has reduced capacity for drug-drug interaction due to diminished P450 inhibition, particularly with respect to CYP3A4 and CYP2C9 (reduced interference with normal metabolism and clearance of co-administered drugs), and possesses improved oral bioavailability and a lower clearance rate in vivo (higher blood concentrations at lower doses). The favorable properties of CEP-37440 in comparison to CEP-28122 are surprising and unexpected.

13-week Oral Toxicity and Toxicokinetic Study of CEP-28122 in Sprague-Dawley Rats, Including a 4-week Recovery Period There were no drug-related deaths during the study and no drug-related effects on body weight, food consumption, or cardiac troponin concentrations. Drug-related effects on hematology parameters were limited to minimal, non-adverse reductions in erythrocytes, hemoglobin and hematocrit in females and minimal, non-adverse increases in platelets in both sexes. Other statistical differences were observed and considered not meaningful due to the magnitude or direction change, and/or the lack of dose-dependency.

Platelets remained mildly elevated in males and females at 150 mg/kg/day at recovery. Possible drug-related effects on coagulation parameters were limited to prolongation of prothrombin time (PT) and partial thromboplastin time (APTT) in males that received 150 mg/kg/day and shortening of AP and APTT in females at all dose levels (values for females remained within expected ranges). There were no meaningful changes evident at the end of the recovery period.

Drug-related changes in clinical chemistry parameters were limited to moderate, but inconsistent increases in alanine aminotransferase (ALT), total bilirubin, aspartate aminotransferase (AST), γ-glutamyltransferase (GGT), and sorbitol dehydrogenase (SDH) among males that received ≥75 mg/kg/day. These effects were more pronounced at the end of the 13 week dosing period than they were at the time of the 4-week interim sample collection and were mostly attributable to effects in a single animal. AST and ALT also were increased in the females that received 150 mg/kg/day but these effects were generally much lower magnitude than observed in the males. Notably, females also exhibited a statistically significant, dose-dependently, and progressive increase in cholesterol at all dose levels. At the end of the recovery period, AST, ALT, and SDH remained elevated in individual males that had received 75 mg/kg/day during the dosing period. AST, ALT, and SDH remained moderately increased in males that had received 150 mg/kg/day during dosing and, to a lesser magnitude, in the females that had received 150 mg/kg/day during dosing.

Total protein and globulins were dose-dependently increased in males that received ≥75 mg/kg/day and in females that received ≥30 mg/kg/day. Albumin also was statistically increased in females that received ≥75 mg/kg/day, but values remained within expected ranges. Statistical increases in calcium were considered secondary to the increased albumin, and total protein. Other sporadic statistical differences were observed at termination and considered not meaningful due to the magnitude or direction of change, and/or the lack of dose-dependency. There were no effects of dosing on total protein, globulin, albumin, or calcium at the end of the recovery period.

Urine volumes increased and specific gravity decreased in males and females at 150 mg/kg/day at termination. No other remarkable changes were observed in urinalysis parameters at termination or recovery.

Increased liver weights (relative to controls) were noted in females that received ≥30 mg/kg/day and in males that received ≥75 mg/kg/day (Males also had decreased thymus weights relative to control at 75 mg/kg/day). Increased kidney, spleen, and adrenal weights were noted in both sexes at dosages ≥75 mg/kg/day. Heart weights also were modestly increased at dosages ≥75 mg/kg/day. However, because there were no correlative microscopic findings in the heart, the toxicological significance of this finding is not clear. Effects in the kidney, heart and spleen of males persisted to the end of the four-week recovery period. There were no persistent drug-related effects evident in females. At the end of the 13-week dosing period, brown or black discoloration of the kidneys was observed macroscopically in males that received 150 mg/kg/day and in females that received 75 mg/kg/day. One male that received 150 mg/kg/day had focus/foci on the kidneys which correlated microscopically to tubular pigment at the end of recovery. At the end of the 13-week dosing period, drug-related microscopic alterations were evident in the kidneys, adrenal glands, liver, lung, brown adipose tissue, mesenteric lymph node, spleen, and thyroid glands of animals that received ≥30 mg/kg/day. Findings in the adrenal glands, liver, lung, brown adipose tissue, mesenteric lymph node, spleen, and thyroid glands are not considered to be adverse due to low severity and substantial evidence of recovery during the 4-week recovery period. Progressive neuropathy, evident in the kidneys of animals that received ≥75 mg/kg/day was considered to be adverse due to due to high prevalence and persistence throughout the 4 week recovery period. Pigmentation, presumed to be accumulated drug, also was evident in several tissues at recovery but is not considered to be adverse.

Minimal to mild swelling of lenticular fibers, especially in the subcapsular axial cortex, was evident in recovery animals that received ≥75 mg/kg/day during the dosing period. This finding corresponded with clinical cataract in these animals. Swelling of lens fibers; however, can be an artifact of fixation with Davidson's fluid resulting from cell swelling associated with acetic acid. Swelling of lens fibers in the subcapsular cortical region was noted in treated animals (including the animals listed above and other treated animals with no record of clinical cataract) and, to a lesser extent, in some control animals in this study. Additionally, swelling of lens fibers in a circumferential, anterior cortical pattern was noted in a few treated animals at 75 and 150 mg/kg/day, but with no corresponding ophthalmoscopic findings, this finding was regarded as artifact secondary to Davidson's fixation. For these reasons, the swelling of lens fibers observed in this study was interpreted as artifact, and was not recorded as a microscopic finding. However, the possibility of a real antemortem change that was masked by the artifacts cannot be completely excluded.

Based on the results noted above, the No Observable Adverse Effect Level (NOAEL) for this study was considered to be 30 mg/kg/day, limited by adverse histopathological effects in the kidney that persisted throughout the 4-week recovery period at dosages ≥75 mg/kg/day.

13-week Oral Toxicity and Toxicokinetic Study of CEP-28122 in Cynomolgus Monkeys with a 6-week Recovery Period The administration of CEP-28122 via daily nasogastric gavage for 91 consecutive days at dose levels of 20, 40, and 80/60 mg/kg resulted in several adverse drug-related events at all dose levels including morbidity and mortality in two animals dosed with 80/60 mg/kg and likely two additional animals (one dosed with 40 mg/kg and the other dosed with 20 mg/kg). There was an additional animal that underwent early necropsy; however, this was not related to CEP-28122 administration. The administration of 80 mg/kg resulted in seizures for 2 animals on Days 9 and/or 10 and led to a dose level reduction to 60 mg/kg in all animals within this group. There were no CEP-28122-related changes in food consumption, body weight, ophthalmic examinations, coagulation parameters, urinalysis parameters, and heart rate, and there were no definitive CEP-28122-related changes in blood pressure or troponin I.

The clinical history for animals that underwent early necropsy could generally be divided into two categories: 1) animals that had a gradual decline in health status over several days/weeks, and 2) animals that appeared clinically to be tolerating the drug until shortly following dosing on the day of early necropsy. For animals in the former category, there were clinical pathology changes suggestive of coagulopathy, acute phase response, severe dehydration, and/or liver toxicity, whereas animals in the latter category were largely absent of clinical pathology changes. Although there was a clinical history of rapid morbidity (within 1-3 minutes of dosing) and death (within 15 minutes of dosing) within category 2 animals was suggestive of drug instillation or aspiration into the lungs, the dose administration into the lungs could not be identified based on histopathology. The reason for the rapid onset of morbidity/mortality was unable to be determined but drug absorbtion from the lungs could not be ruled out.

In the early death animals, drug-related histopathologic findings were identified in the lung, liver, spleen, mesenteric lymph node, and kidney. In the lung, gross and histologic findings consistent with pulmonary edema was identified in all dose groups and were generally more severe than the findings, if any, in animals that survived to Day 92 or 134.

In the surviving animals, there were CEP 28122-related clinical signs present from all dose levels (20, 40, and 80/60 mg/kg) and included: emesis, decreased activity, hunched appearance, and watery feces. In general these clinical signs were not dose dependent (with the exception of watery feces). These clinical signs were not detected during the recovery phase of the study. There were CEP-28122-related increased alanine aminotransferase (ALT) and aspartate aminotransferase (AST) in animals dosed with 80/60 mg/kg suggestive of liver effects; however, these values had returned to baseline by the end of the recovery period. There were no definitive histological correlates in the liver.

CEP-28122-related changes in hematology parameters were limited to a decrease in lymphocytes in animals dosed with 80/60 mg/kg that began on Day 28 and persisted throughout the remaining time points during the dosing phase of the study. Lymphocyte counts had returned to baseline by the end of the recovery period.

On Day 92, drug-related histopathologic findings were identified in the lung, liver, spleen, mesenteric lymph node, and kidney. Histologic findings consistent with pulmonary edema and more chronic lung injury similar to those identified in early death animals were seen at Day 92 and 134, were not dose-proportional, and were generally of lesser incidence and/or severity than the early death animals. Dose-proportional eosinophilic granularity within macrophages in the liver, spleen, and mesenteric lymph nodes was identified typically in animals administered 40 and 80/60 mg/kg CEP-28122 with the inclusion of minimal change in one animal administered 20 mg/kg CEP-28122. This finding was associated with hepatocellular single-cell necrosis in the liver of one high-dose animal, but the increased incidence of the latter at Day 134 and its association with the eosinophilic granularity change suggested an association with administration of the drug. Dose-proportional, brown, granular pigment within tubular epithelium of the kidney was identified in all drug-treatment groups, was minimal to mild as opposed to minimal to moderate in early death animals, and was not associated with degeneration/necrosis of tubular epithelium.

On Day 92, increases in organ weights and/or ratios related to the administration of CEP-28122 were identified for the liver, lung, and kidney of male animals administered 40 and 80/60 mg/kg CEP-28122 (liver and kidney), and 20, 40 and 80/60 mg/kg CEP-28122 (lung). These increases were correlated to eosinophilic granularity within Kupffer cells and hepatocytes in the liver, pulmonary edema in the lung, and brown, pigment accumulation in tubular epithelium in the kidney.

On Day 134, drug-related histopathologic findings were identified in the lung, liver, spleen, mesenteric and mandibular lymph nodes, and kidney. Histologic changes consistent with pulmonary edema were persistent with similar but slightly reduced severity in all dose groups compared to terminal necropsy animals, and were similarly non dose-proportional. Minimal change consistent with more chronic lung injury was present in one high dose animal.

Eosinophilic granularity within macrophages in the liver, spleen, and mesenteric and mandibular lymph nodes was identified typically in animal(s) administered 40 and/or 80/60 mg/kg CEP-28122, and was dose-proportional where more than one group was affected, with the exception of the spleen. This change in the liver was more severe in general than that at Day 92. For the spleen, it was reduced in severity compared to Day 92 for the 80/60 mg/kg group and of variable severity in single occurrences in the 20 and 40 mg/kg groups. The degree of brown, granular pigmentation within areas of eosinophilic granularity within the liver and spleen was generally increased for these recovery groups compared to earlier timepoints. Compared to Day 92, dose-proportional, brown, granular pigment within tubular epithelial cells of the kidney was generally persistent but less severe in animals administered 40 mg/kg CEP-28122, and persistent and more severe in animals administered 80/60 mg/kg CEP-28122. Minimal degeneration/necrosis of tubular epithelium was identified in some animals administered 80/60 mg/kg CEP-28122 with the most severe pigment accumulation.

On Day 134, increases in organ weights and/or ratios related to the administration of CEP-28122 were identified in females for the liver and kidney, were in animals administered 40 and/or 80/60 mg/kg CEP-28122, and were correlated similarly as in terminal necropsy animals.

Pulmonary edema was a significant concern in this study. In many instances the occurrence of pulmonary edema was asymptomatic prior to rapid deterioration and mortality. Additionally, there was no perceptible cardiovascular component to the occurrence of the pulmonary edema, thereby classifying this finding as noncardiogenic pulmonary edema. The rapid onset and lack of a cardiovascular effect would make it very difficult to diagnose or prevent the pulmonary edema in a clinical setting, rendering CEP-28122 unsafe for human use.

4-week Oral Toxicity and Toxicokinetic Study of CEP-28122 in Cynomolgus Monkeys with a 4-week Recovery Period Administration of CEP-28122 by oral gavage once daily for 4 weeks at dose levels of 3, 10, 20, and 40 mg/kg/day did not result in any morbidity or mortality. There were no CEP-28122-related effects on food consumption, body weights, the lung (via auscultation), ocular, ECGs, blood pressure, heart rate, hematology, coagulation, urinalysis, urine chemistry, troponin I, or gross pathology observations at any dose level evaluated.

CEP-28122-related histological effects occurred at dose levels ≥10 mg/kg/day. These findings consisted of minimal or mild, multifocal, increase in vacuolated cells within the lung (presumptive alveolar epithelium) and minimal type II pneumocyte hyperplasia (20 mg/kg/day dose level only). The increased vacuolated cells correlated with an increased lung weight and lung weight ratios from animals at dose levels ≥10 mg/kg/day but did not correlate with any clinical observations or clinical lung findings via auscultation. Following a 4-week recovery period, the increase in vacuolated cells within the lungs was still present in animals at dose levels ≥20 mg/kg/day albeit with a lesser incidence and/or severity. Complete resolution of this finding did occur at the 10 mg/kg/day dose level. The type II pneumocyte hyperplasia was not detected from animals dosed with 20 mg/kg following the 4-week recovery period which also supported a minimal overall decrease in severity.

Possible CEP-28122-related effects included post dose emesis in animals at the 20 and 40 mg/kg dose levels and slight increases in triglycerides (40 mg/kg dose level only). These observations were not detected during the recovery period. Histopathological alterations in the retinal layers in one female dosed with 10 mg/kg/day on Day 29 was considered an uncertain CEP-28122-related effect. There were no correlates in the ophthalmic exam.

This 4-week study at lower doses demonstrated that it would not be possible to avoid lung toxicity with CEP-28122. Especially concerning was the fact that lung damage was occurring without premonitory signs (auscultation). Based upon the occurrence and persistence of lung toxicity in the 4- and 13-week monkey studies, it was concluded that CEP-28122 was too dangerous for human use and development efforts were terminated.

4-week Oral Toxicity and Toxicokinetic Study of CEP-37440 in Sprague-Dawley Rats with a 4-week Recovery Period No drug-related clinical observations were noted during the dosing or recovery phase. Clinical observations appeared rather infrequently, were transient, were with comparable incidences as controls, were associated with moribund animals, were associated with known gavage errors, or occurred in animals whose deaths or sacrifices were not considered drug-related; therefore, clinical observations were not considered drug-related.

Males and females given 30 mg/kg/day gained less weight than controls during all intervals of the dosing phase. During Days 1 to 28 of the dosing phase, males gained 31% less than controls. During Days 1 to 28 of the dosing phase, females gained 65% less than controls. Males and females given 30 mg/kg/day gained as much or more weight than controls during all intervals of the recovery phase. During Days 1 to 28 of the recovery phase, males gained 24% more than controls. During Days 1 to 28 of the recovery phase, females gained 29% more than controls. Males and females given 30 mg/kg/day consumed less food than controls during all intervals of the dosing phase. These differences ranged from 4 to 10% less in males and from 12 to 24% less in females. No drug-related effects on food consumption were noted during the recovery phase. Decreased mean terminal body weight was observed at the terminal sacrifice in males and females given 30 mg/kg/day (0.90× and 0.79×, respectively) and was statistically significant in females.

No drug-related ophthalmic findings were noted during the dosing or recovery phase. No drug-related effects were observed in clinical pathology test results up to 10 mg/kg/day. Several minor clinical pathology effects were observed at 30 mg/kg/day that were minimal to mild in magnitude. None of these findings were considered adverse or toxicologically important.

Drug hematology and coagulation findings at 30 mg/kg/day included the following:
  Mildly lower red cell mass (i.e., red blood cell count, hemoglobin, and hematocrit) in females on Day 29 of the dosing phase
  Mildly lower absolute reticulocyte count in males on Days 15 and 29 of the dosing phase and in females on Day 15 of the dosing phase
  Mildly lower absolute neutrophils count in males on Days 15 and 29 of the dosing phase
  Mildly lower absolute eosinophils count in females on Day 29 of the dosing phase
  Minimally higher fibrinogen in males on Days 15 and 29 of the dosing phase Platelet count appeared unaffected. Decreases in red cell mass, absolute reticulocyte, neutrophils, and eosinophil counts may have reflected mild bone marrow suppression/toxicity but correlative histopathology findings were not observed in the bone marrow. These findings exhibited reversibility at the end of the recovery phase. Higher mean corpuscular volume in females given 30 mg/kg/day at the end of the recovery phase were likely due to higher proportion of younger red cells that typically are larger in size.

Drug-related clinical chemistry findings at 30 mg/kg/day included the following:
  Mildly lower albumin in females on Day 29 of the dosing phase
  Minimally higher globulin in females on Days 15 and 29 of the dosing phase
  Lower albumin-to-globulin ratio in females on Days 15 and 29 of the dosing phase Minimally higher cholesterol in males and females on Days 15 and 29 of the dosing phase Mildly higher serum calcium concentration in males on Day 29 of the dosing phase Minimally lower serum chloride in males and females on Day 29 of the dosing phase Lower albumin and albumin-to-globulin ratio and higher globulin were consistent with inflammation and may have been associated with chronic inflammation of the thoracic cavity observed histologically. Higher cholesterol may have been related to reduced food consumption and body weight gain observed in these animals. Lower serum chloride was likely due to higher urine excretion. A mechanism was not known for higher calcium. No drug-related effect was observed in troponin I concentration at any dose level. All clinical chemistry findings exhibited reversibility at the end of the recovery phase.

Drug-related urine chemistry findings at 30 mg/kg/day included the following:

Minimally higher urine chloride excretion in males and females on Days 15 and 29 of the dosing phase Minimally higher urine fractional clearance for chloride in males and females on Days 15 and 29 of the dosing phase Lower serum chloride was likely associated with higher total excretion and higher fractional clearance of chloride in the urine of animals given 30 mg/kg/day. Correlative histopathology findings were not observed in the kidney of these animals. All urine chemistry findings exhibited reversibility at the end of the recovery phase. No apparent effects were observed in urinalysis test results at any dose level.

Statistically significant or otherwise notable differences in other clinical pathology test results were considered incidental because they were usually of small magnitude, lacked a relationship to dose, or were inconsistent over time and between sexes.

Seven unscheduled deaths occurred in toxicity animals during the dosing phase. None of the unscheduled deaths were attributed to the drug. One control male and one female given 30 mg/kg/day died soon after blood collection; these were considered accidental deaths due to the lack of clinical or anatomical pathology findings suggesting a drug-related effect. Three animals had macroscopic and/or microscopic findings consistent with gavage-related injuries, including one female given 1 mg/kg/day sacrificed in moribund condition on Day 25, one female given 3 mg/kg/day found dead on Day 9, and one female given 10 mg/kg/day sacrificed in moribund condition on Day 25 of the dosing phase. The cause of death was not evident for one male given 30 mg/kg/day found dead on Day 10 and one female given 10 mg/kg/day sacrificed in moribund condition on Day 15 of the dosing phase. All other dosing phase and all recovery toxicity animals survived to their scheduled sacrifice.

At the terminal sacrifice, statistically significant increases in mean organ weights (adjusted for terminal body weight) occurred in the liver of males given 30 mg/kg/day and prostate of males given 10 mg/kg/day. Because these changes lacked microscopic correlates, consistency between sexes (liver only), and/or evidence of a dose response, they were not considered drug-related. Adjusted mean thymus weight was decreased greater than 10% and in a dose-dependent manner in males given 30 mg/kg/day (0.86×) and females given 10 mg/kg/day (0.85×) or 30 mg/kg/day (0.79×). Lacking statistical significance or microscopic correlates, the relationship of thymus weight decreases to the drug in these groups is uncertain. All other organ weight changes at the terminal sacrifice and all organ weight changes at the recovery sacrifice were likely due to normal biologic variation and were not considered a direct effect of the drug.

Macroscopic findings of adhesions in the heart and adhesions or mass in the lung were observed at the terminal sacrifice in females given 30 mg/kg/day, and adhesions in the heart were observed at the recovery sacrifice in one female given 30 mg/kg/day. These macroscopic findings correlated with microscopic findings of fibrosis and/or chronic inflammation in the heart and lung and were considered drug-related. All other macroscopic findings were considered spontaneous, incidental, or associated with accidental death and were not attributed to the drug.

At the terminal sacrifice, microscopic findings consistent with chronic inflammation of the thoracic cavity were present on the serosal surface of the heart and lung and in perithymic connective tissue of females given 30 mg/kg/day. Chronic inflammation and/or fibrosis of the serosal/epicardial surface of the heart and pleural/subpleural surface of the lung was observed in 5/10 females given 30 mg/kg/day. The findings were multifocal to diffuse along the serosal surface of the heart and lung and varied from fibrous thickening with few inflammatory cells to more severe chronic inflammation. Chronic to chronic-active inflammation was also observed in the loose fibrovascular connective tissue surrounding the thymus in 4/10 females given 30 mg/kg/day. At the recovery sacrifice, chronic inflammation and/or fibrosis of the serosal surface of the heart and lung were observed in 2/5 females given 30 mg/kg/day. The findings at the recovery sacrifice were characterized by multifocal to diffuse fibrous thickening of serosal surfaces with little inflammation, suggesting partial resolution. Because findings of chronic inflammation in the thoracic cavity were observed at the scheduled sacrifices in a total of 7/15 females given 30 mg/kg/day and because macroscopic or microscopic evidence of another cause for these findings was lacking, fibrosis and/or inflammation on serosal surfaces of the heart and lung and in perithymic fibroadipose tissue of females given 30 mg/kg/day was considered most likely drug-related and may have resulted from serosal inflammation secondary to pleural and pericardial effusions.

A small increase in incidence of alveolar macrophages in the lung was observed at the terminal sacrifice in females given 30 mg/kg/day and was considered most likely drug-related. An increased incidence of alveolar macrophages was not observed at the recovery sacrifice, suggesting this finding was reversible. All other microscopic findings at scheduled and unscheduled sacrifices were considered spontaneous, incidental, or associated with accidental death and not attributable to the drug.

In a previously conducted 10-day dose range-finding study with CEP-37440, daily administration of the drug by gavage at 10, 30, or 60 mg/kg/day to rats was well tolerated at 10 mg/kg/day. Drug-related adverse findings for body weight in combination with anatomic pathology findings in the bone marrow (hypocellularity); spleen, thymus, and lymph node (decreased lymphocytes); and lung (increase in alveolar macrophages) were observed in animals given ≥30 mg/kg/day. Drug-related changes were not observed in animals given 10 mg/kg/day. In the current study, adverse and drug-related findings were observed in males and females given 30 mg/kg/day. These findings included lower body weight gain in males and females, lower food consumption in males and females, and microscopic findings in females consistent with chronic inflammation of the thoracic cavity.

No drug-related effects were observed in clinical pathology test results up to 10 mg/kg/day. Several minor clinical pathology effects were observed at 30 mg/kg/day that were minimal to mild in magnitude. None of these findings were considered adverse, toxicologically important, or definitively correlated with other adverse inlife or anatomic pathology findings.

Decreases in red cell mass, absolute reticulocyte, neutrophil, and eosinophil counts may have reflected mild bone marrow suppression/toxicity, but correlative histopathology findings were not observed in the bone marrow. These findings exhibited reversibility at the end of the recovery phase. Higher mean corpuscular volume at the end of the recovery phase in females given 30 mg/kg/day was likely due to higher proportion of younger red cells that typically are larger in size.

Lower albumin and albumin-to-globulin ratio and higher globulin were consistent with inflammation and may have been associated with chronic inflammation of the thoracic cavity observed histologically. Higher cholesterol may have been related to reduced food consumption and body weight gain observed in these animals. Lower serum chloride was likely due to higher urine excretion. A mechanism was not known for higher calcium. No drug-related effect was observed in troponin I concentration at any dose level. All clinical chemistry findings exhibited reversibility at the end of the recovery phase.

Lower serum chloride was likely associated with higher total excretion and higher fractional clearance of chloride in the urine of animals given 30 mg/kg/day. Correlative histopathology findings were not observed in the kidney of these animals, and all urine chemistry findings exhibited reversibility at the end of the recovery phase.

In conclusion, oral CEP-37440 administration to rats at doses ≤10 mg/kg/day for 28 days was clinically well tolerated. Microscopic findings consistent with chronic inflammation of the thoracic cavity were present in females given 30 mg/kg/day. Decreases in body weight change and food consumption were present in males and females given 30 mg/kg/day. Based on these findings, the no observed adverse effect level (NOAEL) in this study was 10 mg/kg/day.

4-week Oral Toxicity and Toxicokinetic Study of CEP-37440 in Cynomolgus Monkeys with a 4-week Recovery Period All animals survived until their scheduled sacrifice.

No drug-related clinical observations were noted during the dosing or recovery phase. Clinical observations appeared rather infrequently, were transient, or were with comparable incidences as controls; therefore, they were not considered drug-related.

There was no drug-related effects on body weight or body weight gain noted during the dosing or recovery phase. There were no drug-related abnormal ophthalmic findings noted. Additionally, there were no drug-related observations noted during blood pressure measurements.

No drug-related changes in PR interval, QRS duration, QT interval, corrected QT (QTc) interval, RR interval, or heart rate were observed on Days 3 and 27 of the dosing phase or Day 28 of the recovery phase in animals given 2.5, 7.5, or 20.0 mg CEP-37440/kg of body weight/day (mg/kg/day). No rhythm abnormalities or qualitative ECG changes attributable to CEP-37440 were observed during qualitative assessment of the ECGs.

CEP-37440 administration up to 20.0 mg/kg/day had no effect on clinical pathology test results at the end of dosing or recovery phase.

A few individual animals had clinical pathology findings consistent with inflammation (including slight to notable increases in white blood cell and absolute neutrophils counts, fibrinogen, and C-reactive protein) during the dosing phase, but these animals were usually scattered across all groups, including the control. In that regard, these findings were considered unrelated to the drug because they lacked a dose-related pattern, were often inconsistent over time (especially for leukocyte counts), and involved some control animals.

There were no statistically significant changes in terminal body or organ weights at the terminal sacrifice. All organ weight changes present at the scheduled terminal or recovery sacrifice were attributed to normal biologic variation and considered incidental and unrelated to the drug.

No clear, drug-related macroscopic findings were present at the terminal or recovery sacrifice. At the terminal sacrifice, all (3/3) males given 7.5 mg/kg/day and 2/3 females given 20.0 mg/kg/day exhibited single to few, red to dark red foci on the mucosal surface of the stomach. The serosa of the stomach in one male given 20.0 mg/kg/day exhibited a few red areas. Microscopic correlates were focal hemorrhage within the mucosa and/or submucosa/tunica muscularis, with or without the presence of smooth muscle degeneration within the tunica muscularis. The presence of similar findings in one control female suggests these findings are incidental and unrelated to the drug.

No clear, drug-related microscopic findings were present at the terminal or recovery sacrifice. Macroscopic findings in the mucosa or serosa of the stomach in some animals given CEP-37440 generally correlated with microscopic findings of focal hemorrhage within the mucosa and/or submucosa/tunica muscularis, with or without the presence of smooth muscle degeneration within the tunica muscularis. However, the association of macroscopic and microscopic findings to CEP-37440 administration in the current study is uncertain given the presence of similar and more severe microscopic findings in the stomach of a female given control article and the fact that gastric smooth muscle degeneration is a known background finding in cynomolgus monkeys. Other microscopic findings were present in the stomach of one or more animals, but their association to the drug is uncertain because of their low severity and/or incidence, lack of a clear dose-response, or concurrent presence in a control animal.

All remaining microscopic findings at the terminal or recovery sacrifice, including minimal, focal infiltrates of alveolar macrophages in the lung of two females given 20.0 mg/kg/day, were attributed to normal biologic variation and considered incidental.

In conclusion, oral CEP-37440 administration to cynomolgus monkeys at doses up to 20 mg/kg/day for 28 consecutive days was well tolerated, and no drug-related effects were observed at any dose level. Significantly, there was no evidence whatsoever of pulmonary edema, and CEP-37440 was determined to be safe for use in human trials. The superior safety profile of CEP-37440 in comparison to CEP-28122, and in particular the lack of lung toxicity, was surprising and unexpected.

Figure 4:
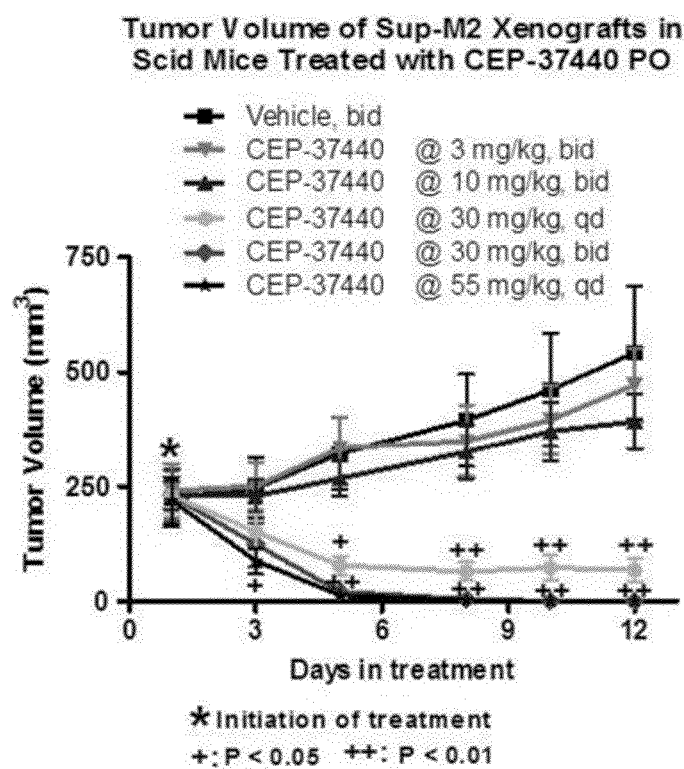
FIG. 4 depicts the anti-tumor efficacy of oral CEP-37440 in Sup-M2 ALCL tumor xenografts in mice.
Figure 5:
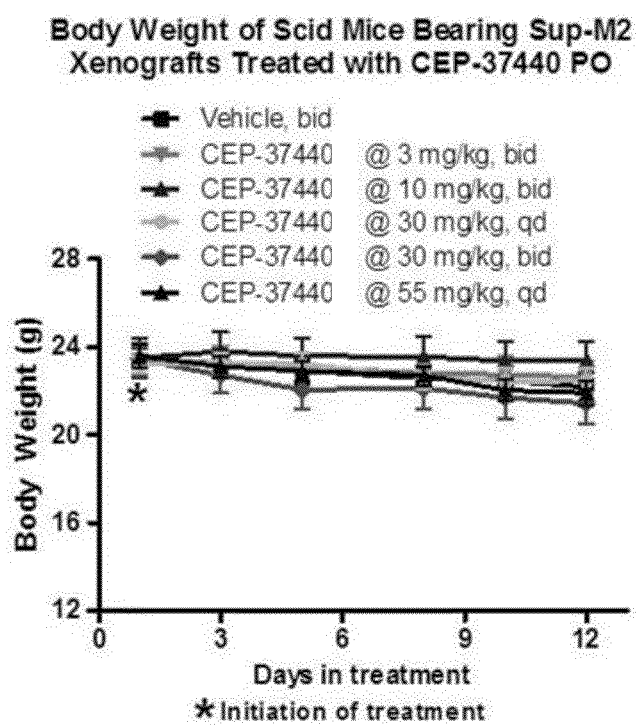
FIG. 5 depicts the body weights of mice bearing Sup-M2 ALCL tumor xenografts dosed orally with CEP-37440.
Figure 6:
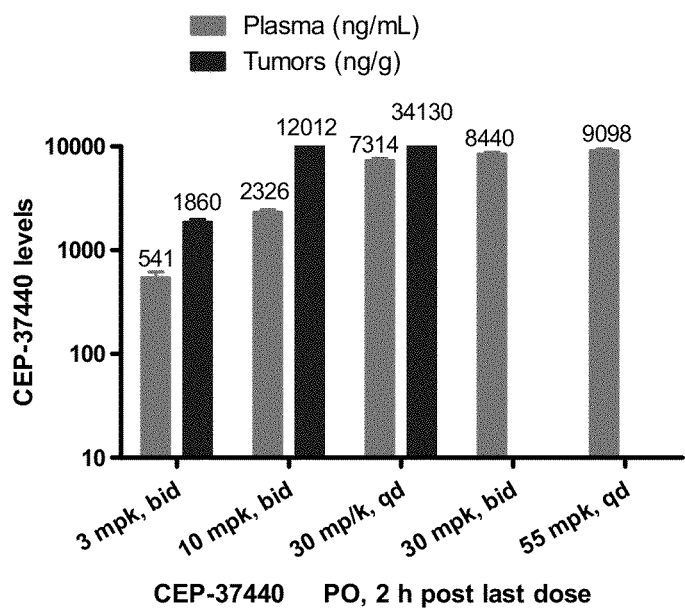
FIG. 6 depicts the plasma and tumor levels of CEP-37440 in mice bearing Sup-M2 ALCL tumor xenografts after oral dosing.

Anti-Tumor Efficacy in NPM-ALK Positive Sup-M2 and Karpas-299 ALCL Tumor Xenograft Models in Mice No significant anti-tumor activity is observed following 12 day treatment with CEP-37440 at 10 mg/kg or lower, bid; partial tumor regression is observed following 12 day treatment with CEP-37440 at 30 mg/kg, qd; complete or near complete tumor regression is observed following 12 day treatment with CEP-37440 at 30 mg/kg bid or 55 mg/kg, qd (FIG. 4). Administration of CEP-37440 is well tolerated with no overt toxicity and no significant compound-related body weight loss of mice at all dosing regimens (FIG. 5). Dose-related levels of CEP-37440 are found in plasma and tumor lysates collected at 2 h post final dosing (FIG. 6). Note that no CEP-37440 is observable in tumors at the 30 mg/kg, bid and 55 mg/kg, qd dosing levels because those animals had no tumors—complete tumor regression. CEP-37440 levels are approximately 2-3-fold higher in plasma and more than 10-fold higher in tumors than the levels at 2 h post single oral dose in PK/PD studies, suggesting some compound accumulation in plasma and tumors with bid or qd oral dosing regimes at 10 and 30 mg/kg.

Figure 7:
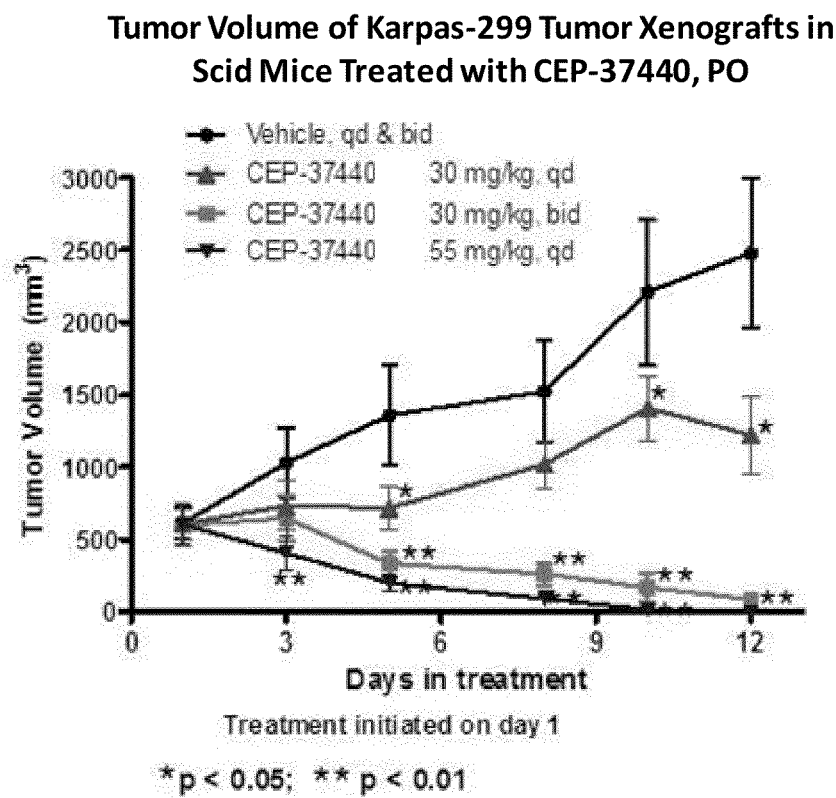
FIG. 7 depicts the anti-tumor efficacy of oral CEP-37440 in Karpas-299 tumor xenografts in mice.
Figure 8:
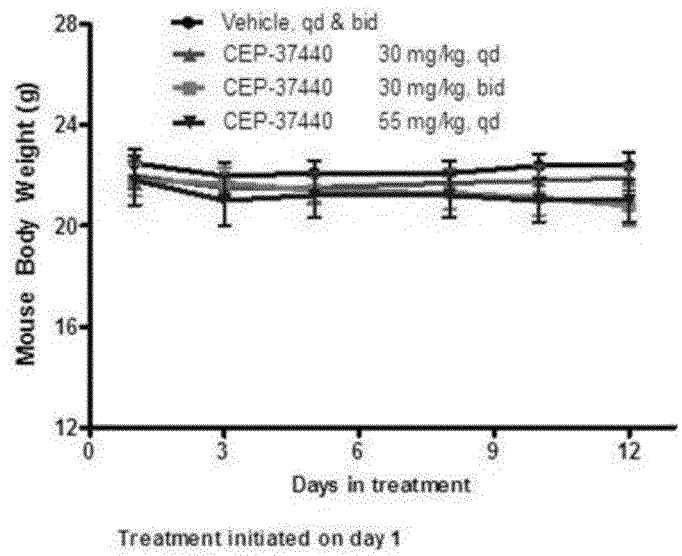
FIG. 8 depicts the body weights of mice bearing Karpas-299 tumor xenografts dosed orally with CEP-37440.
Figure 9:
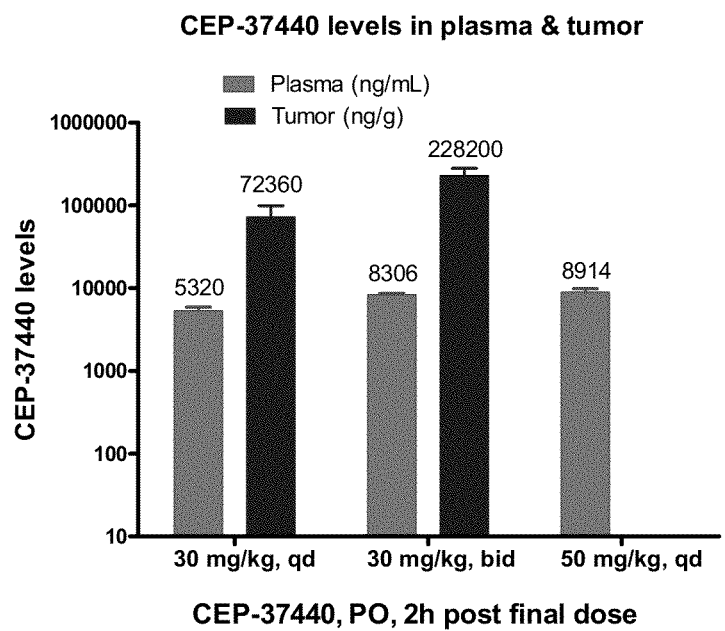
FIG. 9 depicts the plasma and tumor levels of CEP-37440 in mice bearing Karpas-299 tumor xenografts after oral dosing.

In Karpas-299 tumor xenografts, significant anti-tumor activity is observed at 30 mg/kg qd, and complete or near complete tumor regression is observed following 12 day treatment at 30 mg/kg bid or 55 mg/kg, qd (FIG. 7). CEP-37440 administration is well tolerated with no overt toxicity and no significant body weight loss at the dosing regimens (FIG. 8). Dose-related levels of CEP-37440 are observed in plasma and tumor lysates collected at 2 h post final dosing (FIG. 9). Note that no CEP-37440 is observable in tumors at the 50 mg/kg, qd dosing level because those animals had no tumors—complete tumor regression.

Figure 10:
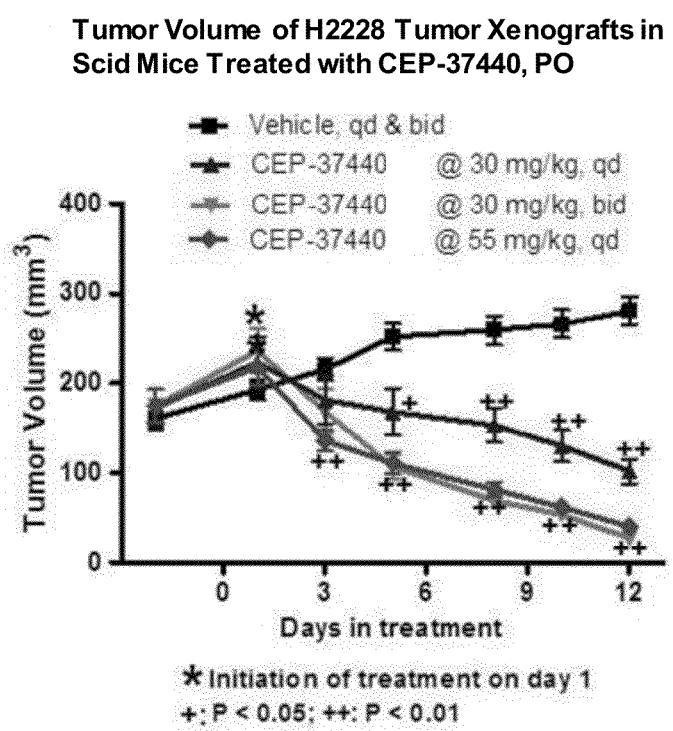
FIG. 10 depicts the anti-tumor efficacy of oral CEP-37440 in NCI-H2228 NSCL tumor xenografts in mice.
Figure 11:
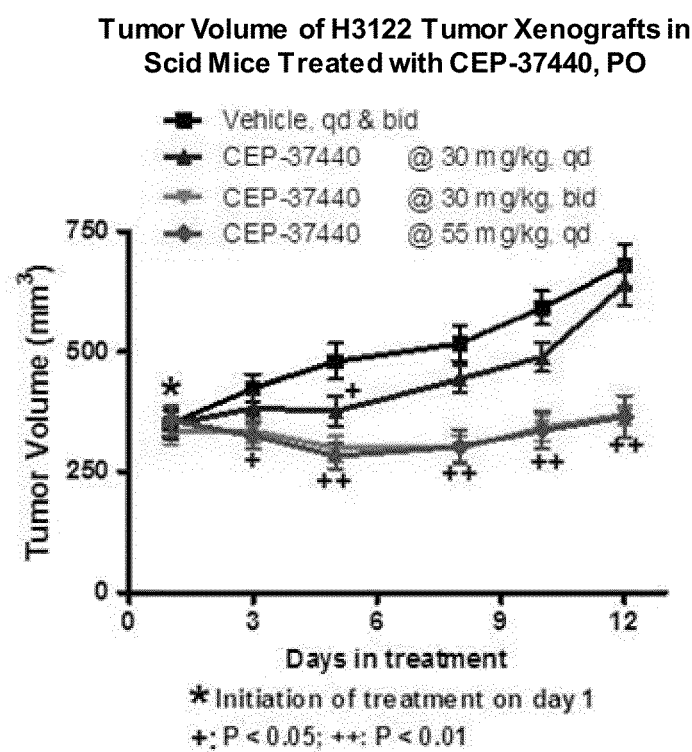
FIG. 11 depicts the anti-tumor efficacy of oral CEP-37440 in NCI-H3122 NSCL tumor xenografts in mice.
Figure 12:
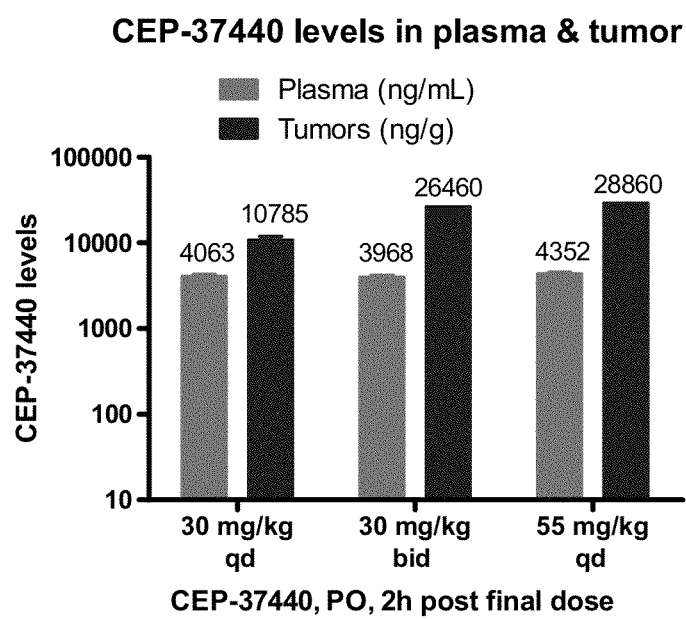
FIG. 12 depicts the plasma and tumor levels of CEP-37440 in mice bearing NCI-H2228 NSCL tumor xenografts after oral dosing.
Figure 13:
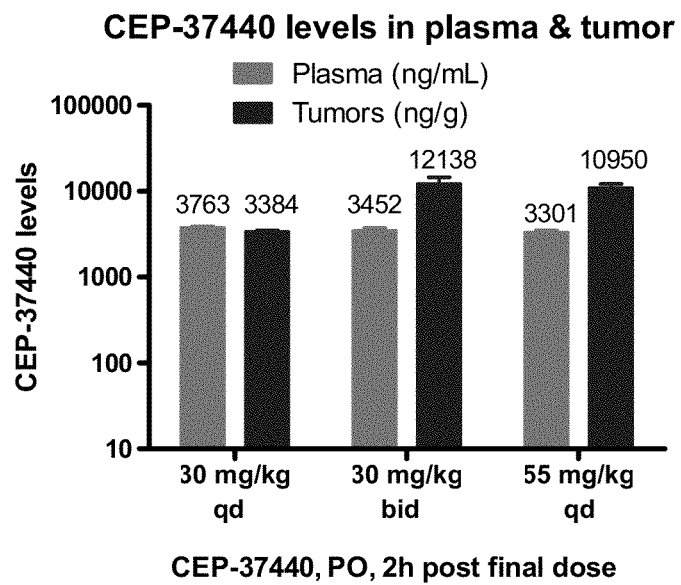
FIG. 13 depicts the plasma and tumor levels of CEP-37440 in mice bearing NCI-H3122 NSCL tumor xenografts after oral dosing.
Figure 14:
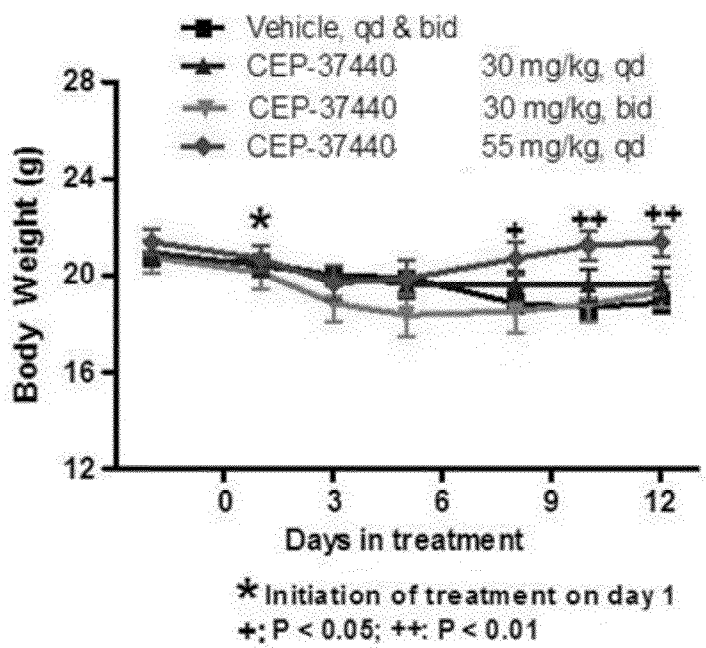
FIG. 14 depicts the body weights of mice bearing NCI-H2228 NSCL tumor xenografts dosed orally with CEP-37440.
Figure 15:
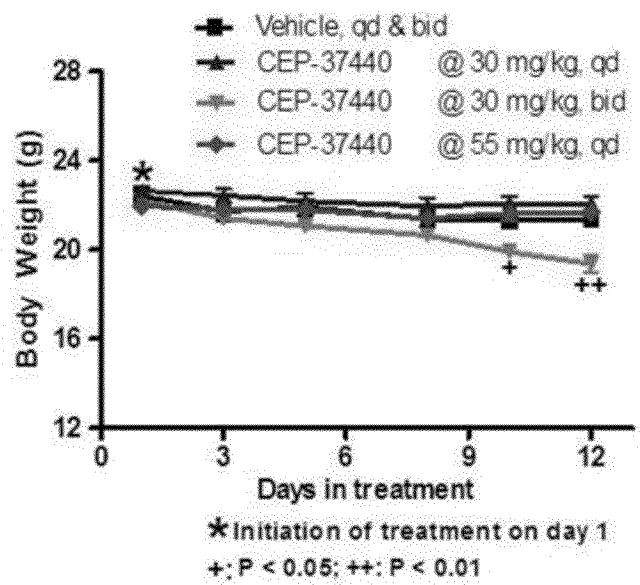
FIG. 15 depicts the body weights of mice bearing NCI-H3122 NSCL tumor xenografts dosed orally with CEP-37440.

Anti-tumor Activity in EML4-ALK Positive (NCI-H2228 and NCI-H3122) NSCLC Tumor Xenografts in Mice with Oral Dosing For the NCI-H2228 tumor xenograft models, treatment with CEP-37440 (HCl salt) at 30 mg/kg, qd and bid and 55 mg/kg, qd po for 12 days results in tumor regressions (FIG. 10). For the NCI-H3122 tumor xenograft models, treatment with CEP-37440 (HCl salt) at 30 mg/kg, bid or 55 mg/kg, qd, po for 12 days results in tumor stasis and partial regressions (FIG. 11). The improved anti-tumor efficacy observed in NCI-H2228 tumor xenografts is likely due to the higher tumor distribution of CEP-37440 (FIGS. 12 and 13). Treatment in these tumor-bearing mice was well tolerated with no overt toxicity or compound-related weight loss (FIGS. 14 and 15), except at 30 mg/kg, bid dose in NCI-H3122 tumor-bearing mice (FIG. 15).

Figure 16:
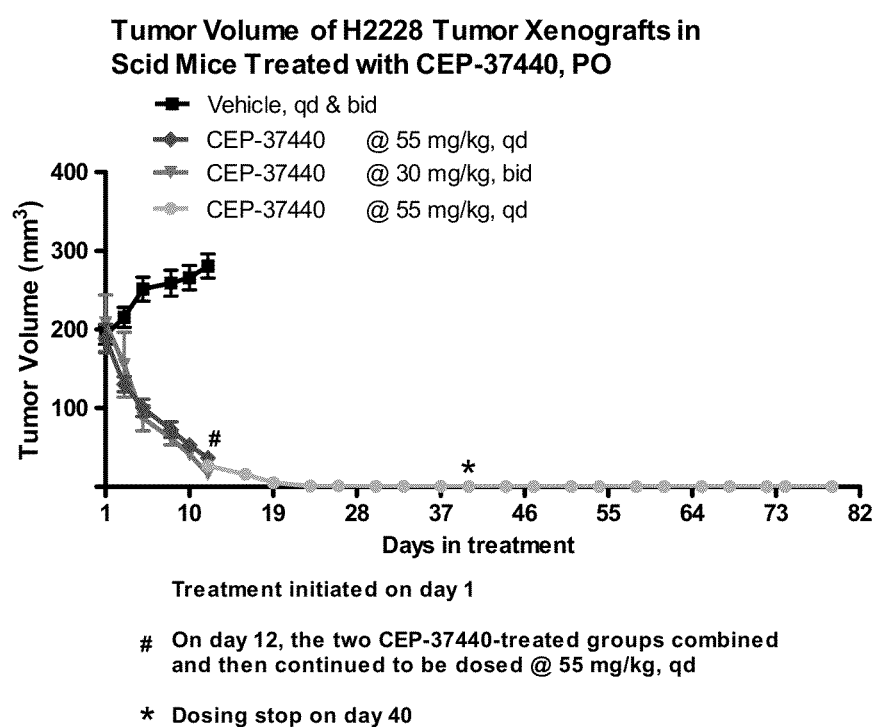
FIG. 16 depicts the anti-tumor efficacy and long term tumor regressions of oral CEP-37440 in NCI-H2228 NSCL tumor xenografts in mice.
Figure 17:
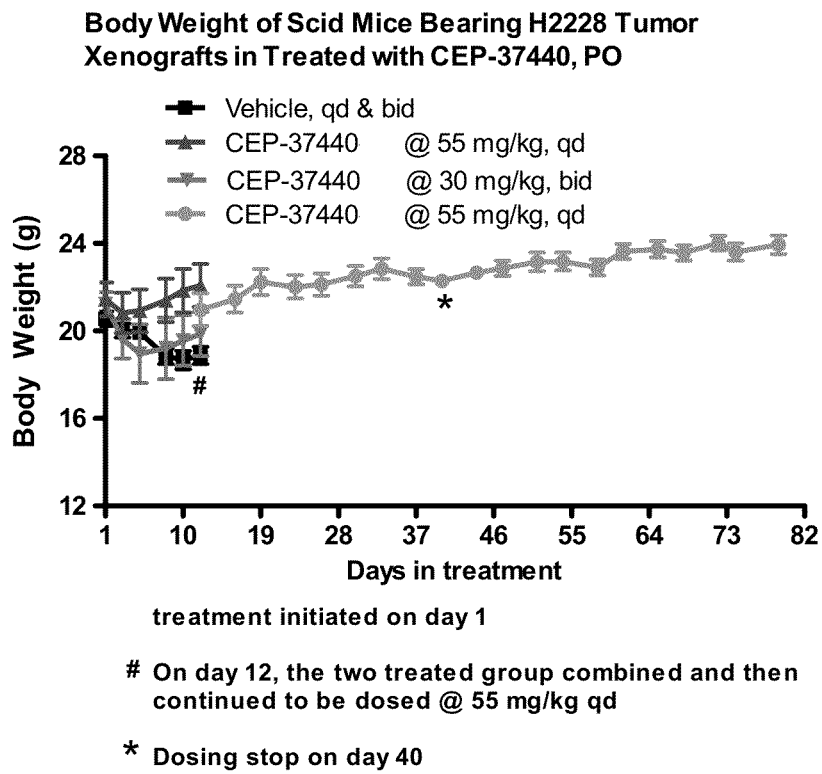
FIG. 17 depicts the body weights of mice bearing NCI-H2228 NSCL tumor xenografts dosed orally with CEP-37440.

Four weeks of additional treatment of the NCI-H2228 tumor-bearing mice at 55 mg/kg qd po provides sustained complete tumor regression in 100% of the animals (FIG. 16). The additional treatment is well tolerated with no overt toxicity and no significant body weight loss (FIG. 17). Sustained tumor regressions are observed in 100% of the mice for 40 days following cessation of treatment, with no tumor re-emergence in any mouse (FIG. 16).

This is important because it suggests that the tumors are completely eradicated and that the mice are effectively "cured" after approximately 6 weeks of treatment with CEP-37440.

Figure 18:
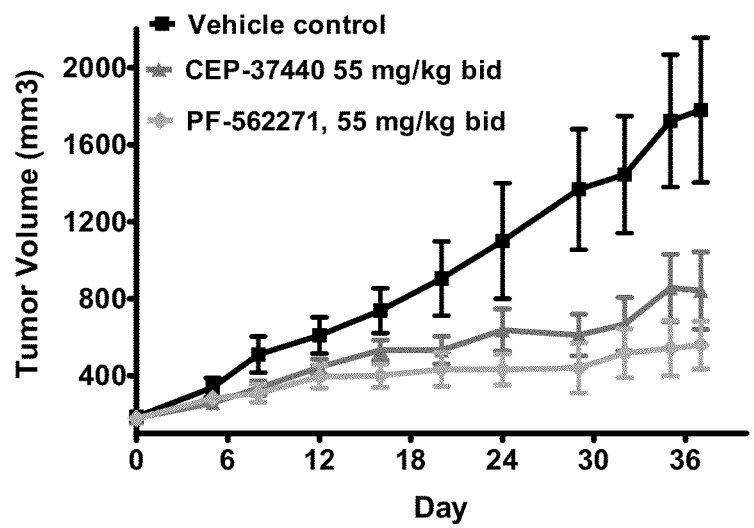
FIG. 18 depicts the anti-tumor efficacy of oral CEP-37440 and PF-562271 in nude mice bearing PC-3 prostate tumor xenografts with constitutive FAK activation.

Anti-Tumor Efficacy Studies in Human Tumor Xenografts of Hormone-independent Prostate Carcinoma, NSCL Carcinoma and HNSC Carcinoma In established FAK-positive PC-3 prostate tumor xenografts, administration of CEP-37440 over a 36 day period results in a 55% tumor growth inhibition (TGI) and 10% incidence of complete tumor regressions, a profile similar to that of an equivalent dose of PF-562271 in this model (69% TGI and 25% incidence of partial tumor regressions) (FIG. 18). All dosing regimens are well tolerated with no overt toxicity or significant body weight loss observed.

Non-small Cell Lung (NSCL) Carcinoma

Figure 19:
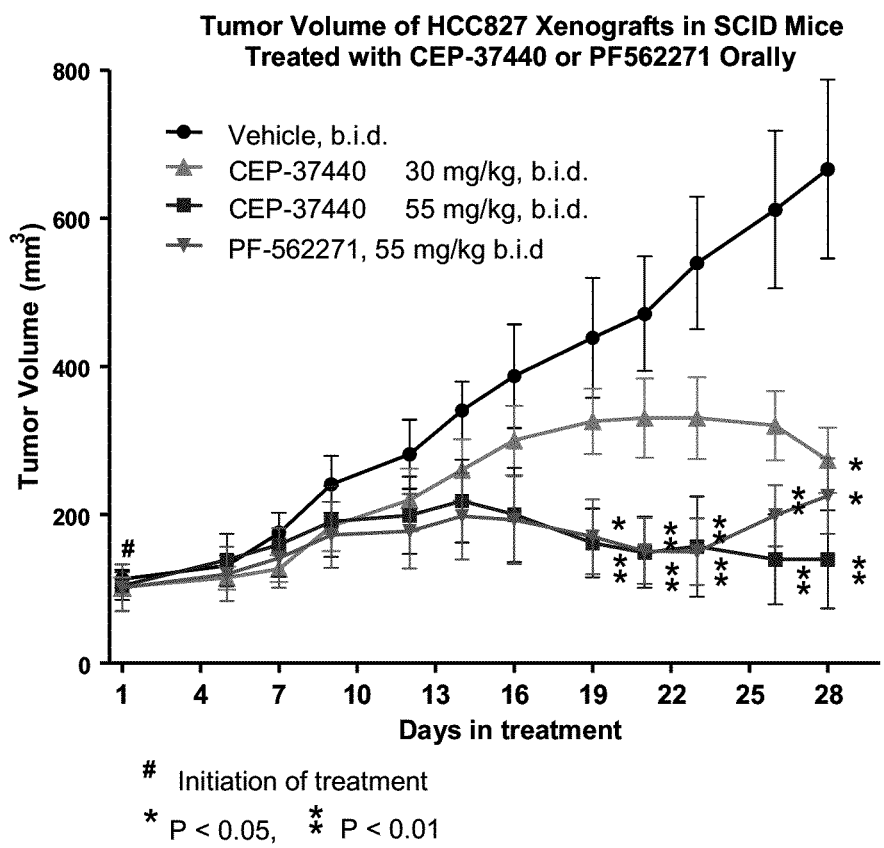
FIG. 19 depicts the anti-tumor efficacy of oral CEP-37440 and PF-562271 in nude mice bearing HCC-827 human NSCL carcinoma xenografts (EML4-ALK negative).
Figure 20:
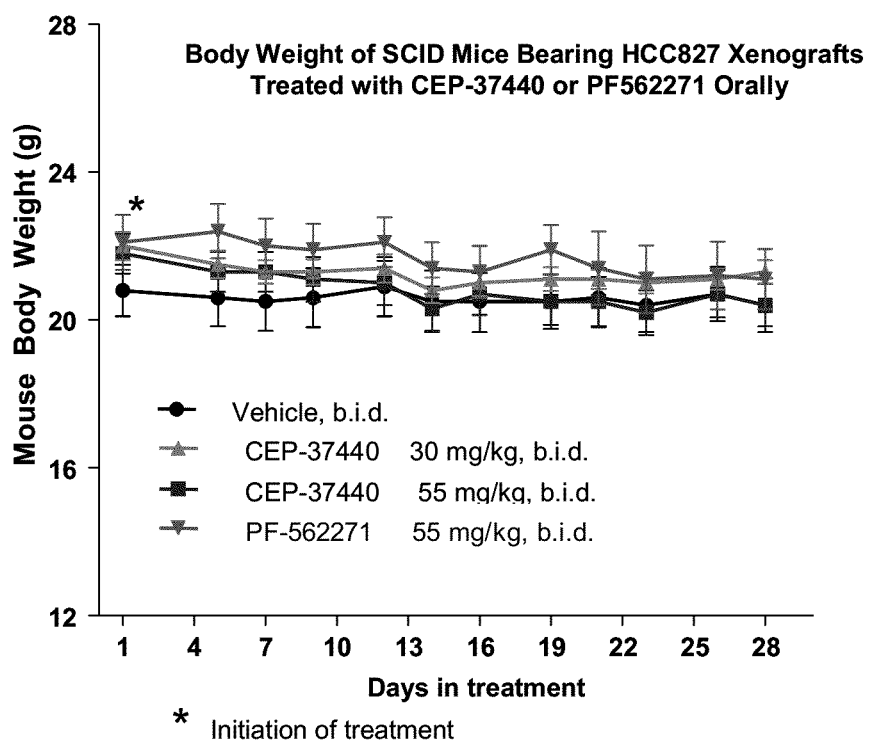
FIG. 20 depicts the body weights of nude mice bearing HCC-827 human NSCL carcinoma xenografts (EML4-ALK negative) dosed orally with CEP-37440 or PF-562271.

CEP-37440 demonstrates dose-related anti-tumor efficacy, with 80% TGI and a 60% incidence of tumor regressions (30% complete and 30% partial) at 55 mg/kg bid and significant efficacy (60% TGI and evidence for partial tumor regression) at 30 mg/kg bid by day 28 of the study (FIG. 19). Significant anti-tumor efficacy (66% TGI) is observed with PF-562271 at 55 mg/kg bid, but modest tumor growth rebound was observed beginning at day 23. Administration of both CEP-37440 and PF-562271 are well tolerated, with no overt toxicity or significant body weight loss observed (FIG. 20). Of note, the significant efficacy achieved with CEP-37440 is not the result of inhibiting EGF-R phosphorylation (activation) in this EML4-ALK negative tumor xenograft model.

Head and Neck Squamous Cell Carcinoma (HNSCC)

Figure 21:
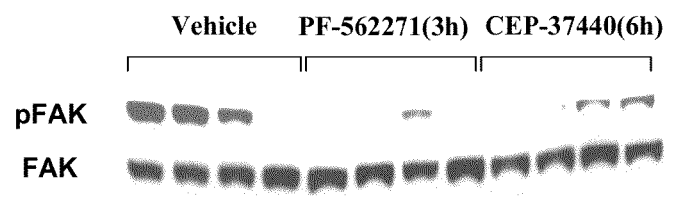
FIG. 21 depicts the tumor pharmacodynamic inhibition of FAK and anti-tumor efficacy of oral CEP-37440 and PF-562271 in SCID mice bearing Detroit 562 human HNSCC carcinoma xenografts (EML4-ALK negative).
Figure 21:
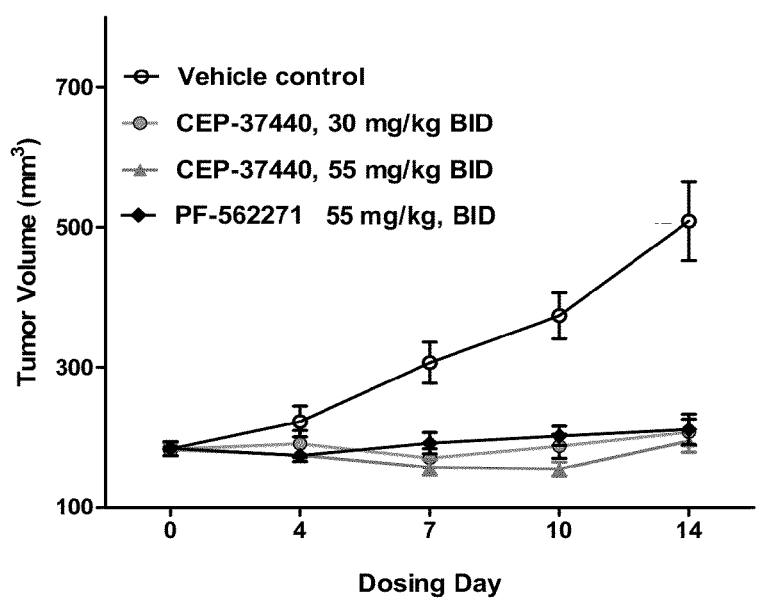

In SCID mice bearing established Detroit 562 HNSCC xenografts, CEP-37440 and PF-562271 demonstrated a clear tumor pharmacodynamic effect for inhibition of FAK activation with no effect on total FAK expression levels (FIG. 21). Over a 28-day period, CEP-37440 and PF-562271 result in tumor stasis and a 20% incidence (CEP-37440, 30 mg/kg bid) and 30% incidence (CEP-37440 and PF-562271, 55 mg/kg bid) of partial tumor regressions. The magnitude of efficacy observed with CEP-37440 (both doses) is comparable to that observed with 55 mg/kg bid of PF-562271 (Roberts et al., 2008). The dosing regimens are well-tolerated with no morbidity or mortality observed.

These studies are important because they show that CEP-37440 demonstrates significant FAK pharmacodynamic inhibition and ALK-independent anti-tumor efficacy in established xenogaft models of hormone-independent prostate carcinoma, NSCL carcinoma, and HNSCC—including objective tumor responses.

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of formula (I)

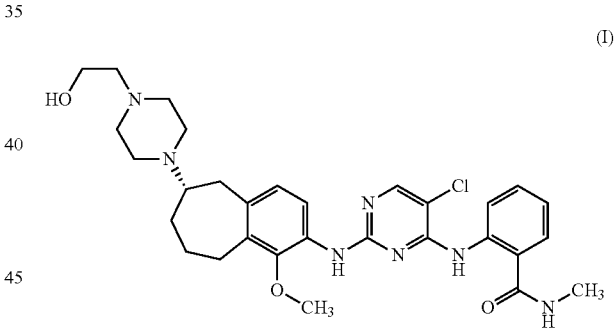

or a salt thereof.

2. The compound of formula I according to claim 1.

3. A salt of the compound of formula (I) according to claim 1.

4. A salt of the compound of formula (I) according to claim 1 wherein the salt is an acid addition salt.

5. A salt of the compound of formula (I) according to claim 1 wherein the salt is an tribenzenesulfonate salt.

6. A tribenzenesulfonate salt of the compound of formula (I) according to claim 5 having a XRPD pattern comprising one or more peaks selected from 7.62±0.2 degrees 2Θ, 13.11±0.2 degrees 2Θ, 13.76±0.2 degrees 2Θ, and 14.05±0.2 degrees 2Θ.

7. A tribenzensulfonate salt of the compound of formula (I) according to claim 5 having a XRPD pattern comprising one or more peaks selected from 6.85±0.2 degrees 2Θ, 7.62±0.2 degrees 2Θ, 8.01±0.2 degrees 2Θ, 13.11±0.2 degrees 2Θ, 13.76±0.2 degrees 2Θ, 14.05±0.2 degrees 2Θ, and 14.60±0.2 degrees 2Θ.

8. A tribenzensulfonate salt of the compound of formula (I) according to claim 5 having a XRPD pattern comprising one or more peaks selected from 7.62±0.2 degrees 2Θ, 13.11±0.2 degrees 2Θ, 13.76±0.2 degrees 2Θ, 14.05±0.2 degrees 2Θ, 17.10±0.2 degrees 2Θ, 17.86±0.2 degrees 2Θ, and 18.10±0.2 degrees 2Θ.

9. A salt of the compound of formula (I) according to claim 1 wherein the salt is a trihydrochloride dihydrate salt.

10. A trihydrochloride dihydrate salt of the compound of formula (I) according to claim 9 having a XRPD pattern comprising one or more peaks selected from 5.42±0.2 degrees 2Θ, 8.86±0.2 degrees 2Θ, 14.06±0.2 degrees 2Θ, 17.52±0.2 degrees 2Θ and 18.51±0.2 degrees 2Θ.

11. A trihydrochloride dihydrate salt of the compound of formula (I) according to claim 9 having a XRPD pattern comprising one or more peaks selected from 5.42±0.2 degrees 2Θ, 5.91±0.2 degrees 2Θ, 8.86±0.2 degrees 2Θ, 10.80±0.2 degrees 2Θ, 11.79±0.2 degrees 2Θ, 14.06±0.2 degrees 2Θ, 14.72±0.2 degrees 2Θ, 17.02±0.2 degrees 2Θ, 17.52±0.2 degrees 2Θ and 18.51±0.2 degrees 2Θ.

12. A pharmaceutical composition comprising a compound or salt according to claim 1 and a pharmaceutically acceptable excipient.

13. The pharmaceutical composition of claim 12, wherein said composition is in the form of a tablet or capsule.

14. A method of treating an ALK- or FAK-mediated condition or disorder in a subject, selected from the group consisting of anaplastic large cell lymphoma (ALCL), non-small cell lung cancer (NSCLC), neuroblastoma, glioblastoma, prostate cancers, squamous cell carcinoma (SCC), and breast cancers comprising the step of administering to the subject a therapeutically effective amount of a compound or a salt of claim 1.

15. The method of claim 14, wherein the ALK- or FAK-mediated condition or disorder is selected from ALK-positive ALCL, EML4-ALK-positive NSCLC, neuroblastoma, glioblastoma, androgen-independent prostate cancers, breast cancers, and head and neck squamous cell carcinomas (HNSCCs).

16. The method of claim 14, wherein the ALK- or FAK-mediated condition or disorder is selected from ALK-positive ALCL, EML4-ALK-positive NSCLC, neuroblastoma, androgen-independent prostate cancers, breast cancers, and HNSCCs.

17. The method of claim 14, wherein the ALK- or FAK-mediated condition or disorder is selected from ALK-positive ALCL, EML4-ALK-positive NSCLC, neuroblastoma, and glioblastoma.

18. The method of claim 14, wherein the ALK- or FAK-mediated condition or disorder is selected from ALK-positive ALCL, EML4-ALK-positive NSCLC, and neuroblastoma.

19. The method of claim 14, wherein the ALK- or FAK-mediated condition or disorder is selected from ALK-positive ALCL and EML4-ALK-positive NSCLC.

20. The method of claim 14, wherein the ALK- or FAK-mediated condition or disorder is selected from androgen-independent prostate cancers, breast cancers, and HNSCCs.

\* \* \* \* \*